(12) United States Patent
Chun et al.

(10) Patent No.: US 11,485,998 B2
(45) Date of Patent: Nov. 1, 2022

(54) SIGNAL EXTRACTION FOR A TARGET NUCLEIC ACID SEQUENCE

(71) Applicant: SEEGENE, INC., Seoul (KR)

(72) Inventors: Jong Yoon Chun, Seoul (KR); Young Jo Lee, Seoul (KR); Han Bit Lee, Seoul (KR)

(73) Assignee: SEEGENE, INC., Seoul (KR)

( * ) Notice: Subject to any disclaimer, the term of this patent is extended or adjusted under 35 U.S.C. 154(b) by 1050 days.

(21) Appl. No.: 16/062,173

(22) PCT Filed: Dec. 15, 2016

(86) PCT No.: PCT/KR2016/014715
§ 371 (c)(1),
(2) Date: Jun. 14, 2018

(87) PCT Pub. No.: WO2017/105104
PCT Pub. Date: Jun. 22, 2017

(65) Prior Publication Data
US 2019/0062824 A1 Feb. 28, 2019

(30) Foreign Application Priority Data
Dec. 15, 2015 (KR) .................. 10-2015-0178868

(51) Int. Cl.
| *C12Q 1/6851* | (2018.01) |
| *C12Q 1/686* | (2018.01) |
| *G16B 25/00* | (2019.01) |
| *G16B 50/00* | (2019.01) |
| *G16B 30/00* | (2019.01) |
| *C12Q 1/682* | (2018.01) |

(52) U.S. Cl.
CPC ........... *C12Q 1/6851* (2013.01); *C12Q 1/686* (2013.01); *G16B 25/00* (2019.02); *G16B 30/00* (2019.02); *G16B 50/00* (2019.02); *C12Q 1/682* (2013.01); *C12Q 2565/401* (2013.01)

(58) Field of Classification Search
CPC ........ G16B 25/00; G16B 30/00; G16B 50/00; C12Q 1/6851; C12Q 1/686
See application file for complete search history.

(56) References Cited

U.S. PATENT DOCUMENTS

| 8,486,622 B2 | 7/2013 | Erikson |
| 2015/0005198 A1 | 1/2015 | Pregibon et al. |

FOREIGN PATENT DOCUMENTS

| EP | 2233587 A1 | 9/2010 |
| JP | 2004028984 A | 1/2004 |
| WO | 2001032922 A2 | 5/2001 |
| WO | 2010013017 A1 | 2/2010 |
| WO | 2012056227 A2 | 5/2012 |
| WO | 2014176575 A1 | 10/2014 |
| WO | 2015147370 A1 | 10/2015 |
| WO | 2015147412 A1 | 10/2015 |
| WO | 2016093619 A1 | 6/2016 |
| WO | 2016093620 A1 | 6/2016 |
| WO | 2016101959 A1 | 6/2016 |

*Primary Examiner* — Jerry Lin
(74) *Attorney, Agent, or Firm* — Gianna Julian-Arnold; Saul Ewing Arnstein & Lehr LLP

(57) ABSTRACT

The present invention relates to extraction of a signal for a target nucleic acid sequence from signals for two target nucleic acid sequences in a sample. The present invention can contribute to dramatic improvement in methods for detecting target nucleic acid sequences using different detection temperatures and reference values. The present invention using an amended reference value as well as an initial reference value can lead to increasing the detection accuracy in methods for detecting target nucleic acid sequences using different detection temperatures and reference values.

22 Claims, 20 Drawing Sheets
Specification includes a Sequence Listing.

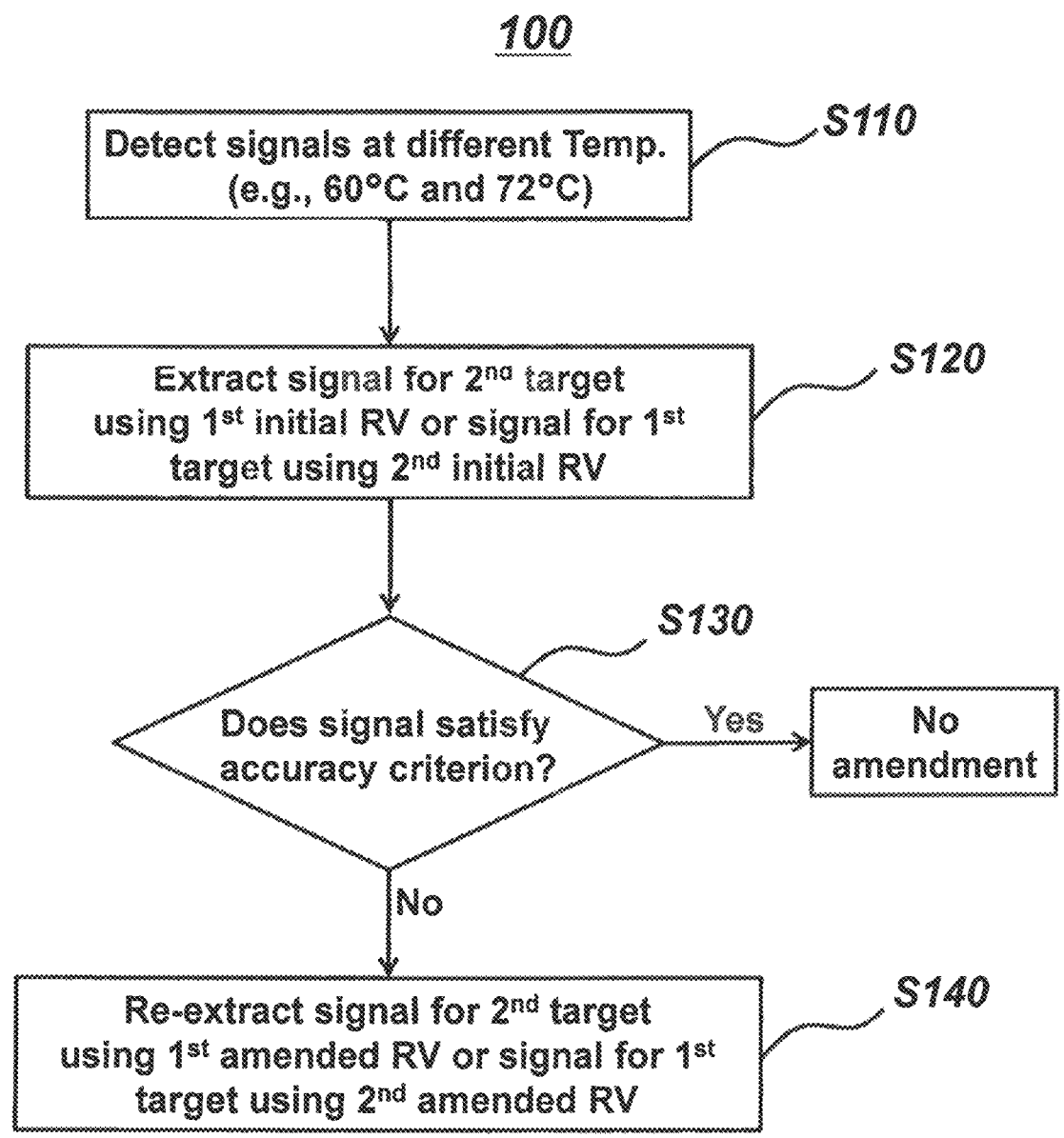

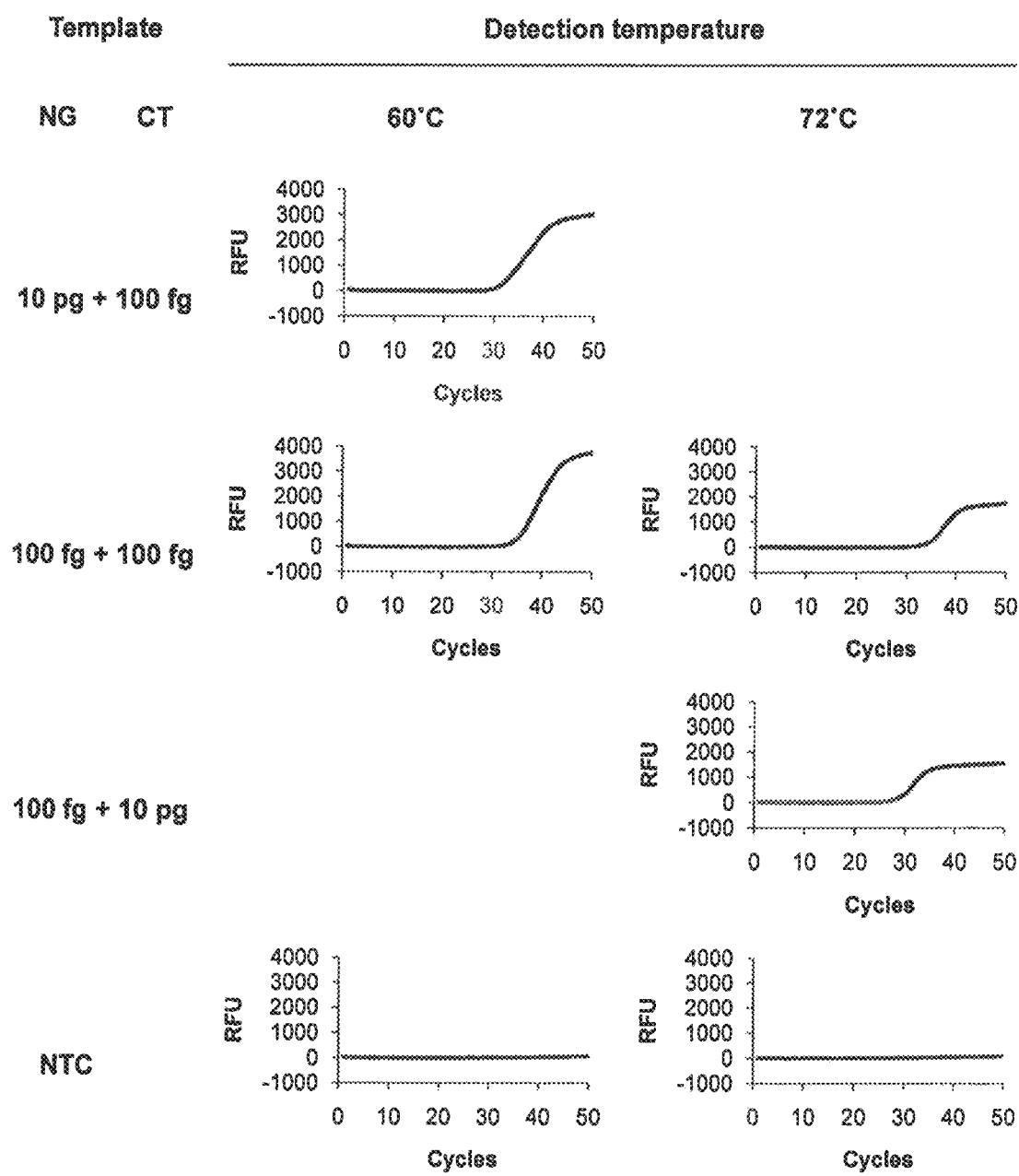

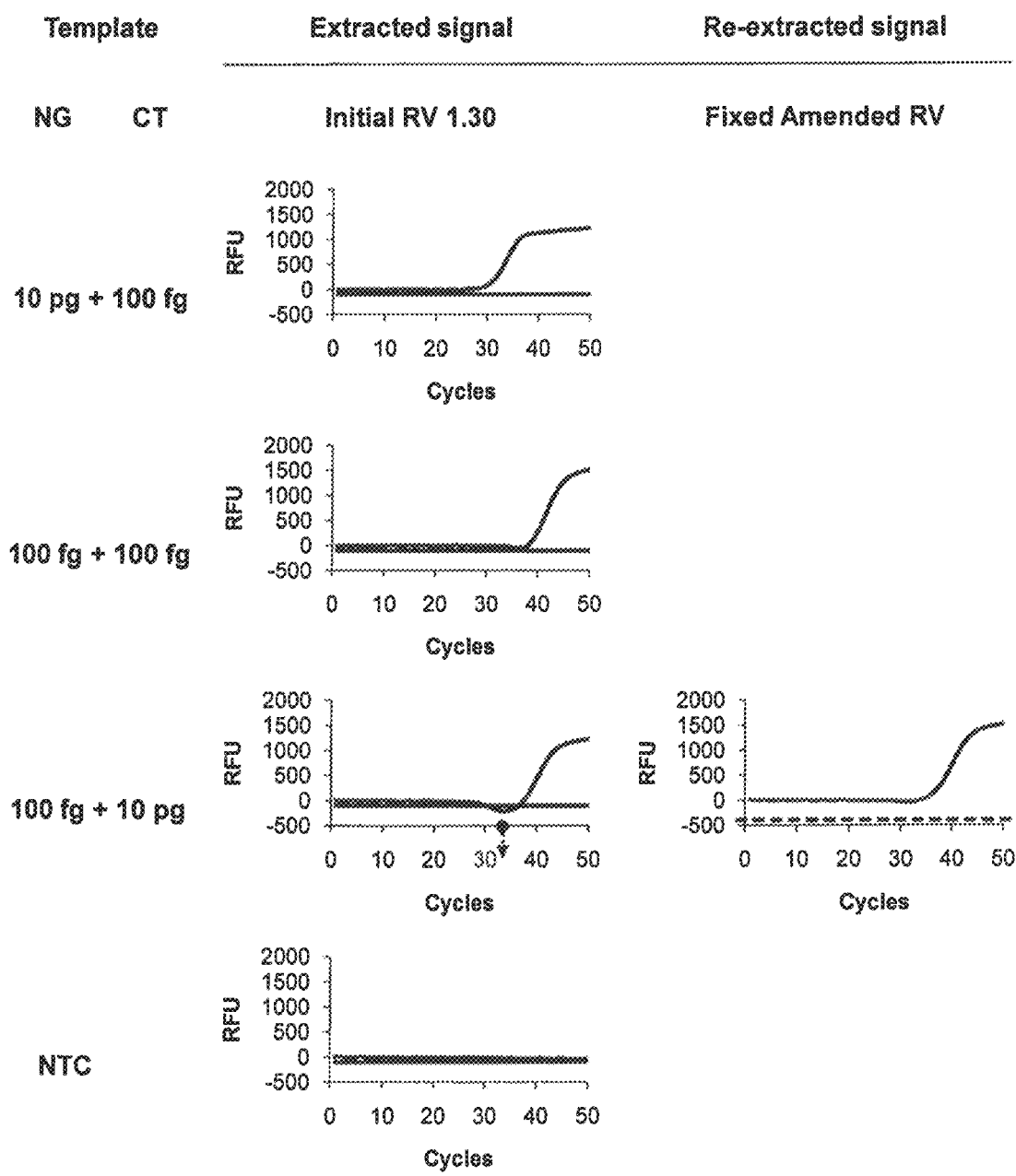

Fig. 4D

| Template | | Initial RV | PARV | Fixed Amended RV |
|---|---|---|---|---|
| NG | CT | | | |
| 10 pg | ~ | 1.30 | ~ | ~ |
| 100 fg | ~ | 1.30 | ~ | ~ |
| ~ | 10 pg | 1.30 | 46 | 1.14 |
| ~ | 100 fg | 1.30 | 50 | 1.14 |
| 10 pg | 100 fg | 1.30 | ~ | ~ |
| 100 fg | 100 fg | 1.30 | ~ | ~ |
| 100 fg | 10 pg | 1.30 | 34 | 1.12 |

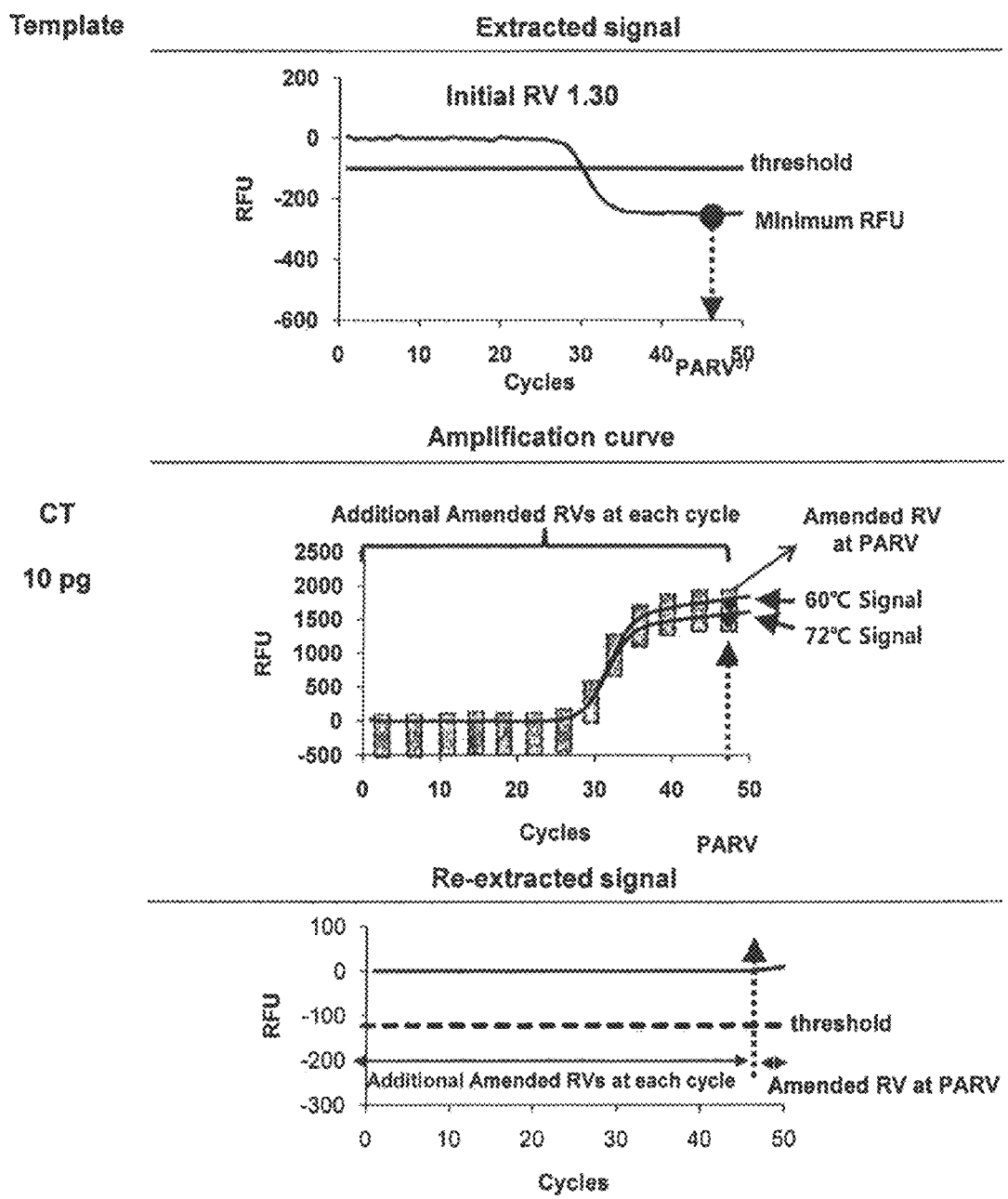

Fig. 5D

| Template | | Initial RV | PARV | Variable Amended RV | |
|---|---|---|---|---|---|
| NG | CT | | | Additional Amended RVs at each cycle | Amended RV at PARV |
| 10 pg | - | 1.30 | - | - | - |
| 100 fg | - | 1.30 | - | - | - |
| - | 10 pg | 1.30 | 46 | Calculated at Each Cycle | 1.14 |
| - | 100 fg | 1.30 | 50 | Calculated at Each Cycle | 1.14 |
| 10 pg | 100 fg | 1.30 | - | - | - |
| 100 fg | 100 fg | 1.30 | - | - | - |
| 100 fg | 10 pg | 1.30 | 34 | Calculated at Each Cycle | 1.12 |

Fig. 7C

| Template | | | PARV | Variable Amended RV | |
|---|---|---|---|---|---|
| NG | CT | Initial RV of CT | | Additional Amended RVs at each cycle | Amended RV at PARV |
| 10 pg | - | 5.00 | - | - | - |
| 1 pg | - | 5.00 | - | - | - |
| - | 10 pg | 5.00 | 48 | Calculated at Each Cycle | 5.67 |
| - | 1 pg | 5.00 | 50 | Calculated at Each Cycle | 6.29 |
| 10 pg | 1 pg | 5.00 | - | - | - |
| 10 pg | 10 pg | 5.00 | - | - | - |
| 1 pg | 10 pg | 5.00 | - | - | - |

Fig. 7F

| Template | | | | Variable Amended RV | |
|---|---|---|---|---|---|
| NG | CT | Initial RV of NG | PARV | Additional Amended RVs at each cycle | Amended RV at PARV |
| 10 pg | - | 2.50 | 50 | Calculated at Each Cycle | 1.72 |
| 1 pg | - | 2.50 | 50 | Calculated at Each Cycle | 1.82 |
| - | 10 pg | 2.50 | - | - | - |
| - | 1 pg | 2.50 | - | - | - |
| 10 pg | 1 pg | 2.50 | 41 | Calculated at Each Cycle | 1.98 |
| 10 pg | 10 pg | 2.50 | 37 | Calculated at Each Cycle | 2.25 |
| 1 pg | 10 pg | 2.50 | - | - | - |

SIGNAL EXTRACTION FOR A TARGET NUCLEIC ACID SEQUENCE

CROSS REFERENCE TO RELATED APPLICATIONS

This application claims priority and the benefit of PCT/KR2016/014715, filed Dec. 15, 2016, Which claims priority and the benefit of KR 10-2015-0178868, filed Dec. 15, 2015, the entire contents of each of which are hereby incorporated in total by reference.

FIELD OF THE INVENTION

The present invention relates to extraction of a signal for a target nucleic acid sequence from signals for two target nucleic acid sequences in a sample.

BACKGROUND OF THE INVENTION

For detection of target nucleic acid sequences, real-time detection methods are widely used to detect target nucleic acid sequences with monitoring target amplification in a real-time manner. The real-time detection methods generally use labeled probes or primers specifically hybridized with target nucleic acid sequences. The exemplified methods by use of hybridization between labeled probes and target nucleic acid sequences include Molecular beacon method using dual-labeled probes with hairpin structure (Tyagi et al, Nature Biotechnology v. 14 MARCH 1996), HyBeacon method (French D J et al., Mol. Cell Probes, 15(6):363-374 (2001)), Hybridization probe method using two probes labeled each of donor and acceptor (Bernad et al, 147-148 Clin Chem 2000; 46) and Lux method using single-labeled oligonucleotides (U.S. Pat. No. 7,537,886). TaqMan method (U.S. Pat. Nos. 5,210,015 and 5,538,848) using dual-labeled probes and its cleavage by 5'-nuclease activity of DNA polymerase is also widely employed in the art.

The exemplified methods using labeled primers include Sunrise primer method (Nazarenko et al, 2516-2521 Nucleic Acids Research, 1997, v. 25 no. 12, and U.S. Pat. No. 6,117,635), Scorpion primer method (Whitcombe et al, 804-807, Nature Biotechnology v. 17 AUGUST 1999 and U.S. Pat. No. 6,326,145) and TSG primer method (WO 2011/078441).

As alternative approaches, real-time detection methods using duplexes formed depending on the presence of target nucleic acid sequences have been proposed: Invader assay (U.S. Pat. Nos. 5,691,142, 6,358,691 and 6,194,149), PTOCE (PTO cleavage AND extension) method (WO 2012/096523), PCE-SH (PTO Cleavage and Extension-Dependent Signaling Oligonucleotide Hybridization) method (WO 2013/115442), PCE-NH (PTO Cleavage and Extension-Dependent Non-Hybridization) method (PCT/KR2013/012312).

The conventional real-time detection technologies described above detect signals generated from fluorescent labels at a selected detection temperature in signal amplification process associated with or with no target amplification. When a plurality of target nucleic acid sequences using a single type of label in a single reaction tube are detected in accordance with the conventional real-time detection technologies, generated signals for target nucleic acid sequences are not differentiated from each other. Therefore, the conventional real-time detection technologies generally employ different types of labels for detecting a plurality of target nucleic acid sequences. The melting analysis using $T_m$ difference permits to detect a plurality of target nucleic acid sequences even using a single type of label. However, the melting analysis has serious shortcomings in that its performance time is longer than real-time technologies and design of probes with different $T_m$ values becomes more difficult upon increasing target sequences.

Accordingly, where novel methods or approaches being not dependent on melting analysis for detecting a plurality of target nucleic acid sequences using a single type of label in a single reaction vessel and a single type of detector are developed, they enable to detect a plurality of target nucleic acid sequences with dramatically enhanced convenience, cost-effectiveness and efficiency. In addition, the combination of the novel methods with other detection methods (e.g., melting analysis) would result in detection of a plurality of target nucleic acid sequences using a single type of label in a single reaction vessel with dramatically enhanced efficiency.

To this end, the present inventors have disclosed a method for detecting a plurality of target nucleic acid sequences using a single type of detector in a single reaction vessel (WO 2015/147412). According to the method, the presence of the target nucleic acid sequence having a relatively low detection temperature can be determined by an analysis of signals detected at a relatively high detection temperature and a relatively low detection temperature. Particularly, based on the finding that the intensities of signals at the relatively low detection temperature and the relatively high detection temperature are different from each other, the present inventors have introduced a reference value representing a relationship of change in signals at different detection temperatures.

Typically, the reference value is predetermined by acquiring a certain range of values via repetitive experiments using a control sample containing only a target nucleic acid sequence having a relatively high detection temperature and then selecting a suitable one among the acquired values. It was observed, however, that erroneous results may often occur when the selected reference value is not suitable in some reactions.

Accordingly, for being free from such erroneous results, there is an urgent need to develop a novel method for extracting a signal for a target nucleic acid sequence in much more accurate manner by amending a reference value.

Throughout this application, various patents and publications are referenced and citations are provided in parentheses. The disclosure of these patents and publications in their entirety are hereby incorporated by references into this application in order to more fully describe this invention and the state of the art to which this invention pertains.

SUMMARY OF THE INVENTION

Accordingly, it is an object of this invention to provide a method for extracting a signal for a target nucleic acid sequence from signals for two target nucleic acid sequences in a sample.

It is another object of this invention to provide a computer readable storage medium containing instructions to configure a processor to perform a method for extracting a signal for a target nucleic acid sequence from signals for two target nucleic acid sequences in a sample.

It is still another object of this invention to provide a device for extracting a signal for a target nucleic acid sequence from signals for two target nucleic acid sequences in a sample.

It is further object of this invention to provide a computer program to be stored on a computer readable storage medium to configure a processor to perform a method for extracting a signal for a target nucleic acid sequence from signals for two target nucleic acid sequences in a sample.

Other objects and advantages of the present invention will become apparent from the detailed description to follow taken in conjugation with the appended claims and drawings.

BRIEF DESCRIPTION OF THE DRAWINGS

FIG. 1 is a flow chart representing an embodiment of this invention for extracting a signal for a target nucleic acid sequence.

FIGS. 2A and 2B represent signals detected at different detection temperatures of 60° C. and 72° C. in accordance with a PTOCE real-time PCR method (MuDT1 Technology), for samples containing genomic DNA of *Neisseria gonorrhoeae* (NG), genomic DNA of *Chlamydia trachomatis* (CT) or mixture of NG and CT.

FIGS. 4B and 4C represent results of signal extraction and re-extraction according to the fixed amended-reference value approach, for samples containing various concentrations of NG, CT or a mixture of NG and CT. A signal extraction was performed by using an initial reference value of 1.30. Where the extracted signal did not satisfy the accuracy criterion, a signal re-extraction was performed in accordance with the fixed amended-reference value approach. In the figure, 'Initial RV' represents the initial reference value for CT; 'Fixed Amended RV' represents the amended reference value for CT calculated by the signals at PARV; and the dotted lines represent the threshold for determining the suitability of the RV from extracted signals.

FIG. 4D represents the initial reference values, PARV and the fixed amended-reference values at PARV applied to each reaction in FIGS. 4B and 4C. In the figure, 'Initial RV' represents the initial reference value for CT; 'PARV' represents the point for setting an amended reference value; and 'Fixed Amended RV' represents the amended reference value for CT calculated by the signals at PARV.

FIG. 5A represents an embodiment of the variable amended-reference value approach for obtaining a re-extracted signal. The extracted signal in FIG. 3 was evaluated whether it satisfied the accuracy criterion (the upper part), a plurality of amended reference values were obtained at a plurality of cycles selected on a basis of the selected PARV (the middle part) and a signal re-extraction was performed by using the plurality of amended reference values (the lower part). In the figure, 'Initial RV' represents the initial reference value for CT; 'threshold' represents the threshold for determining the suitability of the RV from extracted signals; 'PARV' represents the point for setting an amended reference value; 'Amended RVs at each cycle' represents the amended reference values calculated by the signals at each cycle; and 'Amended RV at PARV' represents the amended reference value calculated by the signals at PARV.

FIG. 5D represents the initial reference values, PARV and the variable amended-reference values at PARV applied to each reaction in FIGS. 5B and 5C. In the figure, 'Initial RV' represents the initial reference value for CT; 'PARV' represents the point for setting an amended reference value; 'Additional Amended RVs at each cycle' represents the amended reference values calculated by the signals at each cycle; and 'Amended RV at PARV' represents the amended reference values calculated by the signals at PARV.

FIG. 7C represents the initial reference values, PARV and the variable amended-reference values at PARV applied to the reaction results in FIGS. 7A and 7B. In the figure, 'Initial RV' represents the initial reference value for CT; 'PARV' represents the point for setting an amended reference value; 'Additional Amended RVs at each cycle' represents the amended reference values calculated by the signals at each cycle; and 'Amended RV at PARV' represents the amended reference values calculated by the signals at PARV.

FIG. 7F represents the initial reference values, PARV and the variable amended-reference values at PARV applied to the reaction results in FIGS. 7D and 7E. In the figure, 'Initial RV' represents the initial reference value for NG; 'PARV' represents the point for setting an amended reference value; 'Additional Amended RVs at each cycle' represents the amended reference values calculated by the signals at each cycle; and 'Amended RV at PARV' represents the amended reference values calculated by the signals at PARV.

DETAILED DESCRIPTION OF THIS INVENTION

Figure 2A:
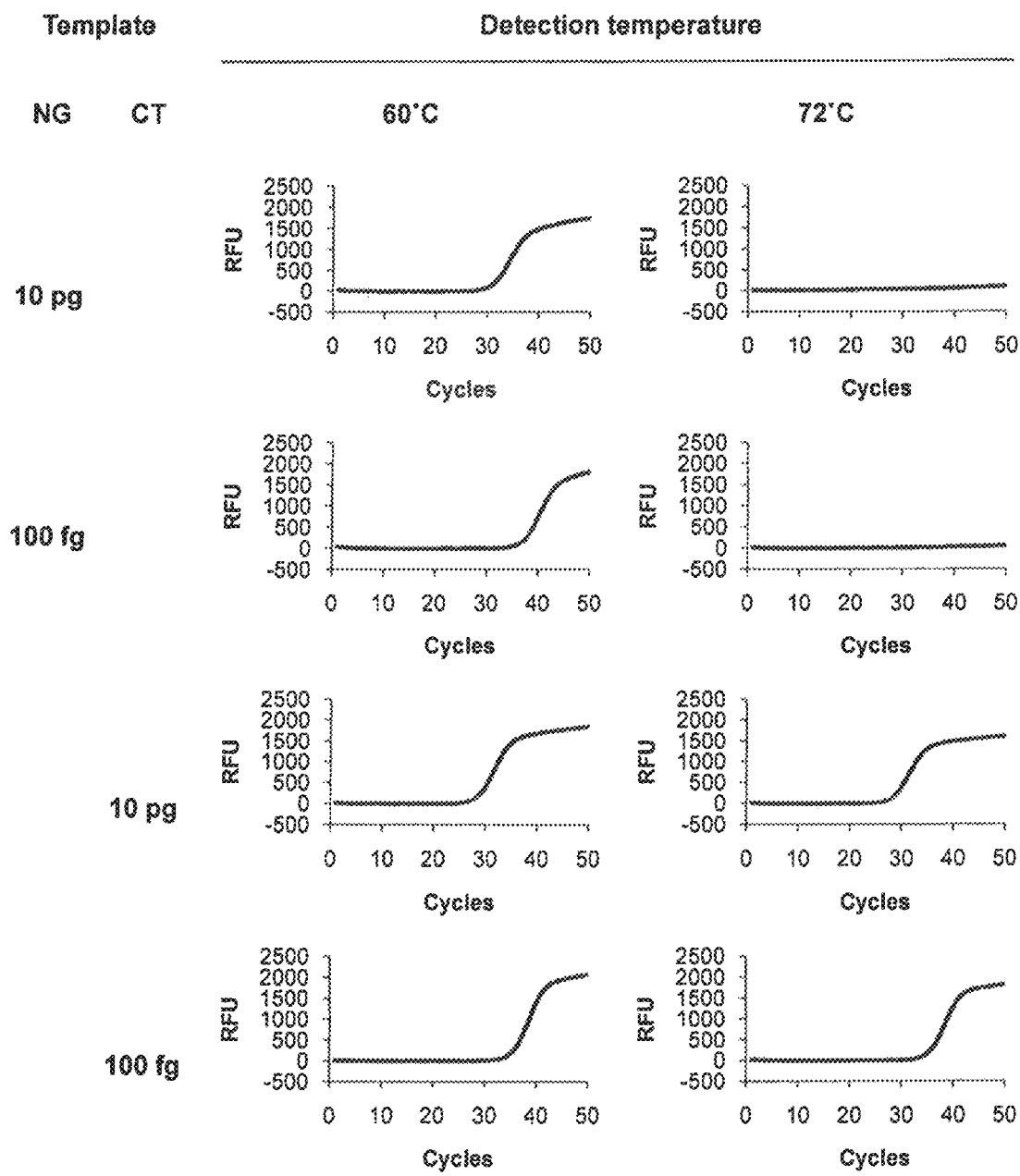

I. Extraction of a Signal for a Target Nucleic Acid Sequence from Signals for Two Target Nucleic Acid Sequences In one aspect of this invention, there is provided a method for extracting a signal for a target nucleic acid sequence from signals for two target nucleic acid sequences in a sample, comprising:

(a) incubating the sample with a first signal-generating means capable of generating a signal for a first target nucleic acid sequence and a second signal-generating means capable of generating a signal for a second target nucleic acid sequence in a single reaction vessel and detecting signals at a relatively high detection temperature and a relatively low detection temperature by the single type of detector; wherein the incubation is performed by a signal-generating process; wherein the detection is performed at one or more cycles of the signal-generating process to obtain a signal value at each of the one or more cycles; wherein the two signals to be generated by the two signal-generating means are not differentiated by a single type of detector;

(b) processing the signal values obtained in the step (a) by using a second initial reference value to extract the signal for the first target nucleic acid sequence or processing the signal values obtained in the step (a) by using a first initial reference value to extract the signal for the second target nucleic acid sequence; wherein the first initial reference value is a value representing a relationship of change in signals provided by the first signal-generating means at the relatively high detection temperature and the relatively low detection temperature, and the second initial reference value is a value representing a relationship of change in signals provided by the second signal-generating means at the relatively high detection temperature and the relatively low detection temperature; wherein the first initial reference value is predetermined from a control reaction using the first target nucleic acid sequence and the first signal-generating means and the second initial reference value is predetermined from a control reaction using the second target nucleic acid sequence and the second signal-generating means; and (c) identifying whether the extracted signal satisfies an accuracy criterion; when the extracted signal does not satisfy the accuracy criterion, the step (b) is repeated using an amended reference value instead of the initial reference value to re-extract the signal for the first target nucleic acid sequence or the second target nucleic acid sequence; wherein the amended reference value is determined such that the re-extracted signal satisfies the accuracy criterion.

The present invention will be described in more detail with reference to the flow chart of FIG. 1 as follows:

Step (a): Incubation and Signal Detection (S110)

In step (a), the sample is incubated with a first signal-generating means capable of generating a signal for a first target nucleic acid sequence and a second signal-generating means capable of generating a signal for a second target nucleic acid sequence in a single reaction vessel. Afterwards, signals at a relatively high detection temperature and a relatively low detection temperature are detected by the single type of detector.

The term "sample" as used herein refers to any material undergoing the method of the present invention. Particularly, the term "sample" refers to any material containing or presumed to contain a nucleic acid of interest (one or both of a first target nucleic acid sequence and a second target nucleic acid sequence) or which is itself a nucleic acid containing or presumed to contain a target nucleic acid sequence of interest. More particularly, the term "sample" as used herein includes biological samples (e.g., cells, tissues, and fluid from a biological source) and non-biological samples (e.g., food, water and soil). The biological samples includes, but not limited to, virus, bacteria, tissue, cell, blood, serum, plasma, lymph, sputum, swab, aspirate, bronchoalveolar lavage fluid, milk, urine, feces, ocular fluid, saliva, semen, brain extracts, spinal cord fluid (SCF), appendix, spleen and tonsillar tissue extracts, amniotic fluid and ascitic fluid. In addition, the sample may include natural-occurring nucleic acid molecules isolated from biological sources and synthetic nucleic acid molecules.

The term used herein "target nucleic acid", "target nucleic acid sequence" or "target sequence" refers to a nucleic acid sequence of interest for analysis, detection or quantification. The target nucleic acid sequence comprises a sequence in a single strand as well as in a double strand. The target nucleic acid sequence comprises a sequence newly generated in reactions as well as a sequence initially present in a sample.

The target nucleic acid sequence may include any DNA (gDNA and cDNA), RNA molecules and their hybrids (chimera nucleic acid). The sequence may be in either a double-stranded or single-stranded form. Where the nucleic acid as starting material is double-stranded, it is preferred to render the two strands into a single-stranded or partially single-stranded form. Methods known to separate strands includes, but not limited to, heating, alkali, formamide, urea and glycoxal treatment, enzymatic methods (e.g., helicase action), and binding proteins. For instance, strand separation can be achieved by heating at temperature ranging from 80° C. to 105° C. General methods for accomplishing this treatment are provided by Joseph Sambrook, et al., *Molecular Cloning, A Laboratory Manual*, Cold Spring Harbor Laboratory Press, Cold Spring Harbor, N.Y. (2001).

The target nucleic acid sequence includes any naturally occurring prokaryotic, eukaryotic (for example, protozoans and parasites, fungi, yeast, higher plants, lower and higher animals, including mammals and humans), viral (for example, Herpes viruses, HIV, influenza virus, Epstein-Barr virus, hepatitis virus, polio virus, etc.), or viroid nucleic acid. The nucleic acid molecule can also be any nucleic acid molecule which has been or can be recombinantly produced or chemically synthesized. Thus, the nucleic acid sequence may or may not be found in nature.

The target nucleic acid sequence should not be construed as limiting the sequence known at a given time or the sequence available as of a given time, but instead should be read to encompass the sequence that may be available or known now or at any time in the future. In other words, the target nucleic acid sequence may or may not be known at the time of practicing the present method. In case of unknown target nucleic acid, its sequence may be determined by one of conventional sequencing methods prior to performing the present method.

The target nucleic acid sequence used in the present invention comprises the first target nucleic acid sequence and the second target nucleic acid sequence. The terms "first target nucleic acid sequence" and "second target nucleic acid sequence" are used herein to distinguish two different target nucleic acid sequences. For instance, the first target nucleic acid sequence and the second target nucleic acid sequence may be two different genes, two different gene regions or two different DNA sequences of interest. Particularly, the first target nucleic acid sequence may be derived from one organism, whereas the second target nucleic acid sequence from another organism.

According to an embodiment of this invention, one of the two target nucleic acid sequences comprise a nucleotide variation, or one of the two target nucleic acid sequences comprises one type of the nucleotide variation and the other comprises the other type of the nucleotide variation.

The term "nucleotide variation" used herein refers to any single or multiple nucleotide substitutions, deletions or insertions in a DNA sequence at a particular location among contiguous DNA segments that are otherwise similar in sequence. Such contiguous DNA segments include a gene or any other portion of a chromosome. These nucleotide variations may be mutant or polymorphic allele variations. For example, the nucleotide variation detected in the present invention includes SNP (single nucleotide polymorphism), mutation, deletion, insertion, substitution and translocation. Exemplified nucleotide variation includes numerous variations in a human genome (e.g., variations in the MTHFR (methylenetetrahydrofolate reductase) gene), variations involved in drug resistance of pathogens and tumorigenesis-causing variations. The term "nucleotide variation" used herein includes any variation at a particular location in a nucleic acid sequence. In other words, the term "nucleotide variation" includes a wild type and its any mutant type at a particular location in a nucleic acid sequence.

According to the present invention, the sample (or target nucleic acid sequences in the sample) is incubated with two signal-generating means in order to obtain signals for the target nucleic acid sequences.

The term "incubating," "incubate," or "incubation" as used herein refers to bring components together for their interaction or reaction. Particularly, the term refers to subjecting the components herein to a signal-generating process.

The term "signal" as used herein refers to a measurable output.

The signal change may serve as an indicator indicating qualitatively or quantitatively the presence or absence of an analyte (a target nucleic acid sequence).

Examples of useful indicators include fluorescence intensity, luminescence intensity, chemiluminescence intensity, bioluminescence intensity, phosphorescence intensity, charge transfer, voltage, current, power, energy, temperature, viscosity, light scatter, radioactive intensity, reflectivity, transmittance and absorbance. The most widely used indicator is fluorescence intensity.

Signals include various signal characteristics from the signal detection, e.g., signal intensity [e.g., RFU (relative fluorescence unit) value or in the case of performing amplification, RFU values at a certain cycle, at selected cycles or at end-point], signal change shape (or pattern) or $C_t$ value, or values obtained by mathematically processing the characteristics.

According to an embodiment, the term "signal" with conjunction with reference value or sample analysis includes not only signals per se obtained at detection temperatures but also a modified signal provided by mathematically processing the signals.

According to an embodiment of this invention, when an amplification curve is obtained by real-time PCR, various signal values (or characteristics) from the amplification curve may be selected and used for determination of target presence (intensity, $C_t$ value or amplification curve data).

The terms "signal for a first target nucleic acid sequence" and "signal for a second target nucleic acid sequence" as used herein refer to signals representing the first target nucleic acid sequence and the second target nucleic acid sequence, respectively. In other words, the terms refer to signals which are generated and detected dependently on the presence of the first target nucleic acid sequence or the second target nucleic acid sequence, and thus a significant level of the signal for a first target nucleic acid sequence or second target nucleic acid sequence indicates the presence of the first target nucleic acid sequence or the second target nucleic acid sequence.

The signal (particularly, the signal intensity) may vary depending upon its detection temperature as well as a signal-generating means employed.

The incubation herein is performed by a signal-generating process using signal-generating means.

The term "signal-generating process" as used herein refers to any process capable of generating signals in a dependent manner on the presence of a target nucleic acid sequence in a sample.

The term "signal-generating means" as used herein refers to any material used in generation of signals indicating the presence of target nucleic acid sequences, for example including oligonucleotides, labels and enzymes. Alternatively, the term used herein "signal-generating means" can be used to refer to any methods using the materials for signal generation.

In particular, the terms "first signal-generating means" and "second signal-generating means" as used herein refer to means for generating signals for a first target nucleic acid sequence and a second target nucleic acid sequence, respectively. The first signal-generating means and the second signal-generating means may include common components (e.g., a single type of label and a single type of enzyme) or different components (e.g., different types of oligonucleotides) used in signal generation. In particular, the first signal-generating means and the second signal-generating means are characterized by having a single type of label (the same label). Thus, the signal derived from the label of the first signal-generating means is not differentiated from the signal derived from the label of the second signal-generating means by conventional methods.

A wide variety of the signal-generating means have been known to one of skill in the art. The signal-generating means include both labels per se and oligonucleotides with labels. The labels may include a fluorescent label, a luminescent label, a chemiluminescent label, an electrochemical label and a metal label. The label per se may serve as signal-generating means, for example, an intercalating dye. Alternatively, a single label or an interactive dual label containing a donor molecule and an acceptor molecule may be used as signal-generating means in the form of linkage to at least one oligonucleotide.

The signal-generating means may comprise additional components for generating signals such as nucleolytic enzymes (e.g., 5'-nucleases and 3'-nucleases).

The signal-generating process is accompanied with signal change. The signal change may serve as an indicator indicating qualitatively or quantitatively the presence or absence of a target nucleic acid sequence.

The details of "signal-generating process" are disclosed in WO 2015/147412 filed by the present inventors, the teachings of which are incorporated herein by reference in its entirety.

According to an embodiment, the signal-generating process is a signal amplification process.

According to an embodiment of this invention, the signal-generating process is a process with amplification or with no amplification of a target nucleic acid sequence.

Particularly, the signal-generating process is a process with amplification of a target nucleic acid molecule. More particularly, the signal-generating process is a process with amplification of a target nucleic acid molecule and capable of increasing or decreasing signals (particularly, increasing signals) upon amplifying the target nucleic acid molecule.

The term used herein "signal generation" include appearance or disappearance of signals and increase or decrease in signals. Particularly, the term "signal generation" means increase in signals.

The signal-generating process may be performed in accordance with a multitude of methods known to one of skill in the art. The methods include TaqMan™ probe method (U.S. Pat. No. 5,210,015), Molecular Beacon method (Tyagi et al., Nature Biotechnology, 14 (3):303(1996)), Scorpion method (Whitcombe et al., Nature Biotechnology 17:804-807 (1999)), Sunrise or Amplifluor method (Nazarenko et al., Nucleic Acids Research, 25(12):2516-2521(1997), and U.S. Pat. No. 6,117,635), Lux method (U.S. Pat. No. 7,537,886), CPT (Duck P, et al., Biotechniques, 9:142-148(1990)), LNA method (U.S. Pat. No. 6,977,295), Plexor method (Sherrill C B, et al., Journal of the American Chemical Society, 126: 4550-4556(2004)), Hybeacons™ (D. J. French, et al., Molecular and Cellular Probes (2001) 13, 363-374 and U.S. Pat. No. 7,348,141), Dual-labeled, self-quenched probe (U.S. Pat. No. 5,876,930), Hybridization probe (Bernard P S, et al., Clin Chem 2000, 46, 147-148), PTOCE (PTO cleavage and extension) method (WO 2012/096523), PCE-SH (PTO Cleavage and Extension-Dependent Signaling Oligonucleotide Hybridization) method (WO 2013/115442) and PCE-NH (PTO Cleavage and Extension-Dependent Non-Hybridization) method (PCT/KR2013/012312) and CER method (WO 2011/037306).

When the signal-generating process is performed in accordance with TaqMan™ probe method, the signal-generation means may comprise a primer pair, a probe with an interactive dual label and DNA polymerase having 5' to 3' nuclease activity. When the signal-generating process is performed in accordance with PTOCE method, the signal-generation means may comprise a primer pair, PTO (Probing and Tagging Oligonucleotide), CTO (Capturing and Templating Oligonucleotide) and DNA polymerase having 5' to 3' nuclease activity. Either PTO or CTO may be labeled with suitable labels.

According to an embodiment, the signal-generating process is performed in a process involving signal amplification together with target amplification.

According to an embodiment, the amplification reaction as the signal-generating process is performed in such a manner that signals are amplified simultaneously with amplification of the target nucleic acid sequence (e.g., real-time PCR). Alternatively, the amplification reaction is performed in such a manner that signals are amplified with no amplification of the target nucleic acid molecule [e.g., CPT method (Duck P, et al., Biotechniques, 9:142-148 (1990)), Invader assay (U.S. Pat. Nos. 6,358,691 and 6,194, 149)].

A multitude of methods have been known for amplification of a target nucleic acid molecule, including, but not limited to, PCR (polymerase chain reaction), LCR (ligase chain reaction, see Wiedmann M, et al., "Ligase chain reaction (LCR)—overview and applications." PCR Methods and Applications 1994 February; 3(4):S51-64), GLCR (gap filling LCR, see WO 90/01069, EP 439182 and WO 93/00447), Q-beta (Q-beta replicase amplification, see Cahill P, et al., Clin Chem., 37(9):1482-5(1991), U.S. Pat. No. 5,556,751), SDA (strand displacement amplification, see G T Walker et al., Nucleic Acids Res. 20(7):16911696 (1992), EP 497272), NASBA (nucleic acid sequence-based amplification, see Compton, J. Nature 350(6313):912 (1991)), TMA (Transcription-Mediated Amplification, see Hofmann W P et al., J Clin Virol. 32(4):289-93(2005); U.S. Pat. No. 5,888,779) or RCA (Rolling Circle Amplification, see Hutchison C. A. et al., Proc. Natl Acad. Sci. USA. 102:1733217336 (2005)).

After incubation of the sample, signals from the two signal-generating means (i.e., first signal generating means and second-signal generating means) are detected at a relatively high detection temperature and a relatively low detection temperature.

The present invention may be performed by using any type of signal-generating means in view of detection temperatures. One of the two signal-generating means may be designed to provide signals at both of the two detection temperatures and the other designed to provide signals only at the relatively low detection temperature in the presence of a target nucleic acid sequence. Alternatively, the two signal-generating means all may be designed to provide signals at both of the two detection temperatures in the presence of a target nucleic acid sequence.

According to an embodiment, the detection temperatures are predetermined in considering a temperature range to allow for signal generation by the signal-generating means. The detection temperatures comprise the relatively high detection temperature (e.g., 72° C.) and the relatively low detection temperature (e.g., 60° C.).

According to an embodiment, the relatively high detection temperature is a temperature capable of generating a signal for the target nucleic acid sequence having the relatively high detection temperature, and the relatively low detection temperature is a temperature capable of generating both of a signal for the target nucleic acid sequence having the relatively low detection temperature and a signal for the target nucleic acid sequence having the relatively high detection temperature.

According to another embodiment, the relatively high detection temperature and the relatively low detection temperature are those capable of generating both of a signal for the target nucleic acid sequence having the relatively low detection temperature and a signal for the target nucleic acid sequence having the relatively high detection temperature.

One of features of the present invention is to determine differentially the presence of the two target nucleic acid sequences by detecting at different detection temperatures signals indicative of the presence of the two target nucleic acid sequences.

According to an embodiment, the detection temperatures for target nucleic acid sequences are predetermined in considering a temperature range to allow signal generation by the signal-generating means.

The present invention uses that there is a certain temperature range to allow signal generation in a dependent manner on signal-generating means.

For example, when a signal-generating means generates a signal upon hybridization (or association) between two nucleic acid molecules and do not generate a signal upon non-hybridization (or dissociation) between them, a signal is generated at temperatures allowing hybridization between two nucleic acid molecules, however, no signal is generated at temperatures failing to hybridize between two nucleic acid molecules. As such, there is a certain temperature range to allow signal generation i.e., signal detection) and other temperature range not to allow signal generation. The temperature ranges are affected by the Tm value of the hybrid of the two nucleic acid molecules employed in the signal-generation means.

Considering the two temperature ranges, a detection temperature may be determined for each of the target nucleic acid sequences. A relatively high detection temperature can be selected from the former temperature range, and the relatively high detection temperature is assigned to the first target nucleic acid sequence. A relatively low detection temperature can be selected from the latter temperature range, and the relatively low detection temperature is assigned to the second target nucleic acid.

The important technical feature of the present invention is to extract the signal for the second target nucleic acid sequence or the signal for the first target nucleic acid sequence, by analyzing both the signal at the relatively high detection temperature and the signal at the relatively low detection temperature.

The detection of signals is carried out in a detector, particularly a single type of detector.

The term "a single type of detector" as used herein means a detection means for a single type of signal. In a detector comprising several channels (e.g., photodiodes) for several different types of signals, each channel (e.g., a photodiode) corresponds to "a single type of detector".

According to an embodiment of this invention, the two signal-generating means comprise an identical label and signals from the label are not differentiated by the single type of detector.

The detection of signals from the two signal-generating means at a relatively high detection temperature and a relatively low detection temperature is performed at one or more cycles of the signal-generating process to obtain a signal value at each of the one or more cycles.

The term used herein "cycle" refers to a unit of changes of conditions in a plurality of measurements accompanied with changes of conditions. For example, the changes of conditions include changes in temperature, reaction time, reaction number, concentration, pH and/or replication number of a target nucleic acid molecule sequence. Therefore, the cycle may include time or process cycle, unit operation cycle and reproductive cycle. For example, an isothermal amplification allows for a plurality of measurements for a sample in the course of reaction time under isothermal conditions and the reaction time may correspond to the changes of conditions and a unit of the reaction time may correspond to a cycle.

Particularly, when repeating a series of reactions or repeating a reaction with a time interval, the term "cycle" refers to a unit of the repetition.

For example, in a polymerase chain reaction (PCR), a cycle refers to a reaction unit comprising denaturation of a target molecule, annealing (hybridization) between the target molecule and primers and primer extension. The increases in the repetition of reactions may correspond to the changes of conditions and a unit of the repetition may correspond to a cycle.

The detection of signals provides a signal value at each cycle of the signal-generating process. The term used herein "signal value" means either signal value actually measured at each cycle of the signal-generating process (e.g., actual value of fluorescence intensity processed by amplification reaction) or its modification. The modification may include mathematically processed value of measured signal value (e.g., intensities). Examples of mathematically processed value of measured signal value may include logarithmic value and derivative of measured signal values. The term used herein "signal" is intended to encompass the term "signal value" and therefore these terms will be used interchangeably.

The signals generated by the two signal-generating means are not differentiated by a single type of detector. The term "signals not differentiated by a single type of detector" means that signals are not differentiated from each other at a certain detection temperature by a single type of detector due to their identical or substantially identical signal properties (e.g., optical properties, emission wavelength and electrical signal).

The term used herein "a single type of signal" means signals providing identical or substantially identical signal properties (e.g., optical properties, emission wavelength and electrical signal). For example, FAM and CAL Fluor 610 provide different types of signals from one another.

The signals are generated by the signal-generating process, thereby providing a data set. The term used herein "data set" refers to a set of data points. The term used herein "data point" means a coordinate value comprising a cycle and a signal value at the cycle. Data points obtained by the signal-generating process may be plotted with coordinate values in a rectangular coordinate system, giving a curve (e.g., amplification curve). The curve may be a fitted or normalized (e.g., baseline-subtracted) curve. In particular, the signals detected are plotted against cycles.

In a particular embodiment, the signals, and the data sets, the data points and the curve thereof are baseline-subtracted.

Step (b): Processing Signal Values for Extraction of a Signal for a Target Nucleic Acid Sequence (S120)

Afterwards, the signal values obtained in the step (a) are processed by using a second initial reference value to extract the signal for the first target nucleic acid sequence or processed by using a first initial reference value to extract the signal for the second target nucleic acid sequence.

The term "reference value" as used herein describes a relationship or degree of change in signals, a signal change or a signal difference, in particular numerically, when two signals are generated at different detection temperatures (i.e., relatively high detection temperature and relatively low detection temperature). Stated otherwise, the "reference value" includes any value reflecting a pattern (rule) of a signal change at different detection temperatures. Also, the term "reference value" indicates a value representing the degree of change between a signal detected at relatively high detection temperature and a signal detected at relatively low detection temperature for a particular target nucleic acid sequence. The reference value may indicate a value used herein to transform, convert, adjust or modify a signal detected at one temperature into a signal at another temperature. The reference value may vary depending upon the types of the target nucleic acid sequences, the types of the signal-generating means and the conditions of incubation and detection. Thus, a variety of reference values may be determined for different or same target nucleic acid sequences.

The reference value may be expressed in various aspects. For example, the reference value may be expressed as numerical values, the presence/absence of signal or plot with signal characteristics.

The term "reference value" is further described herein as "first initial reference value", "second initial reference value", "first amended reference value", "second amended reference value". In the terms, the terms "first" and "second" are used for distinguishing reference values for the first target nucleic acid sequence and second target nucleic acid sequence, respectively. The terms "initial" and "amended" are used for distinguishing a reference value for initial signal extraction and a reference value for re-extraction of signal, respectively.

Particularly, the terms "first initial reference value" and "second initial reference value" as used herein refer to reference values which are predetermined for the first target nucleic acid sequence and for the second target nucleic acid sequence, respectively and which are initially used in the signal extraction of the second target nucleic acid sequence and of the first target nucleic acid in step (b), respectively.

More particularly, the first initial reference value is a value representing a relationship of change in two signals provided by the first signal-generating means at the relatively high detection temperature and the relatively low detection temperature, and the second initial reference value is a value representing a relationship of change in two signals provided by the second signal-generating means at the relatively high detection temperature and the relatively low detection temperature.

Meanwhile, the terms "first amended reference value" and "second amended reference value" used in the following step (c) refer to reference values that substitute for the first initial reference value and the second initial reference value, respectively, when erroneous signals are extracted, which are then used to re-extract signals for the second target nucleic acid sequence and the first target nucleic acid sequence.

In an embodiment, the reference value may be determined considering a signal value at a selected cycle. In other words, the reference value may be determined considering a signal value at a selected cycle among signals detected at a relatively high detection temperature and at a relatively low detection temperature. In such case, the selected cycle, may be one of cycles following a baseline region of an amplification curve, particularly one of cycles in a plateau region, more particularly an end cycle.

In an alternative embodiment, the reference value may be determined considering a plurality of signal values at different selected cycles. For instance, the reference value may be determined considering a mean of a plurality of signal values at different selected cycles.

The reference values will be described in detail below. The reference values should be interpreted as comprising the initial reference values as well as the amended reference values.

Initial reference value may be predetermined by incubating a corresponding target nucleic acid sequence with a signal-generating means, detecting signals at a relatively high detection temperature and a relatively low detection temperature, and then obtaining a relationship of change in signals detected at the relatively high detection temperature and the relatively low detection temperature.

According to an embodiment, the initial reference value is predetermined by using a standard material corresponding to a target nucleic acid sequence.

According to an embodiment, the initial reference value is predetermined from a control reaction. For example, the first initial reference value is predetermined from a control reaction using the first target nucleic acid sequence and the first signal-generating means and the second initial reference value is predetermined from a control reaction using the second target nucleic acid sequence and the second signal-generating means.

According to an embodiment, the initial reference value may be predetermined by using a control sample containing a corresponding target nucleic acid sequence. For instance, the first initial reference value may be predetermined by using a control sample containing the first target nucleic acid sequence and the second initial reference value may be predetermined by using a control sample containing the second target nucleic acid sequence.

The initial reference value may be predetermined by acquiring a certain range of values via iterative reactions for the control reaction (or control sample) under various conditions (e.g., concentrations of a target nucleic acid sequence and types of primers) and selecting a suitable one among the acquired values.

In an embodiment, the initial reference value may be selected such that a signal for a target nucleic acid sequence not to be extracted is eliminated. In other embodiments, the initial reference value may be selected such that a signal for a target nucleic acid sequence to be extracted is not eliminated or eliminated as little as possible. In another embodiment, the initial reference value may be selected such that signal for a target nucleic acid sequence not to be extracted is eliminated and signal for a target nucleic acid sequence to be extracted is not eliminated or eliminated as little as possible.

For example, where one intends to extract a signal for a first target nucleic acid sequence by using a second initial reference value, the second initial reference value may be selected such that the signal for the second target nucleic acid sequence is eliminated and the signal for the first target nucleic acid sequence is not eliminated.

More specifically, when the target nucleic acid sequences comprise "*Chlamydia trachomatis* (CT)" and "*Neisseria gonorrhoeae* (NG)" and a signal for "NG" is intended to be extracted, the initial reference value for CT may be selected such that the signal for CT is completely eliminated and the signal for NG is not eliminated or eliminated as little as possible.

The reference value may be empirically obtained by repetitive experiments.

The reference value may be selected among a certain range empirically obtained by repetitive experiments. In this regard, it is advantageous that a relatively high value within the range is selected as an initial reference value, because the relatively high initial reference value has a higher propensity to eliminate a signal intended not to be extracted, compared to relatively low initial reference values. For example, when a range from 1.1 to 1.50 is obtained, a value around 1.50 may be more suitable as an initial reference value. Alternatively, a value exceeding the range may be selected as an initial reference value. For example, a value of 5%, 10%, 20%, 30%, 40%, 50%, 60%, 70%, 80%, 90% or 100% greater than the upper limit of the range may be selected an initial reference value. However, it is noted that too high initial reference value is not desirable, since it may rather eliminate a signal intended to be extracted.

According to an embodiment, the initial reference value can be calculated by the difference between signals provided by a corresponding signal-generating means at the relatively high detection temperature and the relatively low detection temperature.

According to an embodiment, the initial reference value can be calculated by mathematically processing the signals provided by a corresponding signal-generating means at the relatively high detection temperature and the relatively low detection temperature.

In certain embodiment, the mathematical processing includes calculation (e.g., addition, multiplication, subtraction and division) using signals or other values derived from signals.

According to an embodiment of this invention, the mathematical processing of the signals to obtain the initial reference value is a calculation of a ratio of the signal provided by a corresponding signal-generating means at the relatively low detection temperature to the signal provided by a corresponding signal-generating means at the relatively high detection temperature. According to an embodiment of this invention, the mathematical processing of the signals to obtain the initial reference value is a calculation of a ratio of the signal provided by a corresponding signal-generating means at the relatively high detection temperature to the signal provided by a corresponding signal-generating means at the relatively low detection temperature.

The ratio may be a ratio of a signal value at a cycle of signals detected at the relatively low detection temperature to a signal value at the cycle of signals detected at the relatively high detection temperature. Alternatively, the ratio may be a ratio of a signal value at a cycle of signals detected at the relatively high detection temperature to a signal value at the cycle of signals detected at the relatively low detection temperature. The cycle selected for ratio calculation may be one of cycles following a baseline region of an amplification curve. Particularly, the cycle for ratio calculation may be one of cycles in a plateau region. More particularly, the cycle for ratio calculation may be the end cycle.

In an embodiment, the initial reference value can be obtained by a mean of ratios at several cycles, e.g., consecutive two cycles, three cycles, four cycles, five cycles, etc. Further, the initial reference value can be suitably selected in consideration of ratios at several cycles. For example, the initial reference value can be selected as being a slightly higher than a ratio of a signal value at a cycle or ratios of signal values at several cycles.

In a particular embodiment, the initial reference value may be calculated in accordance with the mathematical equation III:

Initial reference value for a target=[signal at the relatively low temperature for a sample containing only the target]÷[signal at the relatively high temperature for a sample containing only the target] <Equation III>

The mathematical processing for obtaining the initial reference value may be carried out in various fashions. The mathematical processing may be carried out by use of a machine. For example, the signals may undergo a mathematical processing by a processor in a detector or real-time PCR device. Alternatively, the signals may manually undergo a mathematical processing particularly according to a predetermined algorithm.

According to an embodiment of this invention, signal-generating means for the initial reference value may be the same as that for the step (a).

According to an embodiment, the processing of the signal values in the step (b) is carried out by eliminating the signal for the second target nucleic acid sequence from the signals obtained in the step (a) by the second initial reference value or eliminating the signal for the first target nucleic acid sequence from the signals obtained in the step (a) by the first initial reference value.

More particularly, the elimination of the signal generated by the second signal generating means is to mathematically eliminate the signal for the second target nucleic acid sequence from the signals obtained in the step (a) and the elimination of the signal generated by the first signal generating means is to mathematically eliminate the signal for the first target nucleic acid sequence from the signals obtained in the step (a).

Still more particularly, the elimination of the signal generated by the second (or first) signal generating means is to mathematically eliminate the signal for the second (or first) target nucleic acid sequence from the signal detected at a relatively low temperature, or to mathematically eliminate the signal for the second (or first) target nucleic acid sequence from the signal detected at a relatively high temperature.

The present inventors developed two technologies for detecting multiple target nucleic acid sequences in a sample using different detection temperatures. In the former technology, the first signal-generating means generates signals both at the relatively high detection temperature and the relatively low detection temperature and the second signal-generating means generates a signal at the relatively low detection temperature (see WO 2015/147412). In the latter technology, both the first signal-generating means and the second signal-generating means generate signals both at the relatively high detection temperature and the relatively low detection temperature. The former and latter technologies are called as MuDT1 and MuDT2 technologies, respectively.

Where the present invention is applied to the MuDT1 technology, it may be performed as follows:

According to an embodiment, the first signal-generating means generates signals at the relatively high detection temperature and the relatively low detection temperature and the second signal-generating means generates a signal at the relatively low detection temperature, and the processing of the signal values in the step (b) is performed using the first initial reference value to extract the signal for the second target nucleic acid sequence from the signal at the relatively low detection temperature obtained in the step (a).

More particularly, the extraction of the signal for the second target nucleic acid sequence may be performed by the following mathematical equation I-1:

Extracted signal for the second target nucleic acid sequence=[signal at the relatively low detection temperature obtained in the step (a)]−[(signal at the relatively high detection temperature obtained in the step (a))×(the first initial reference value)]; <Equation I-1> wherein the first initial reference value is a ratio of the signal provided by the first signal-generating means at the relatively low detection temperature to the signal provided by the first signal-generating means at the relatively high detection temperature.

In the mathematical equations described herein, the symbol "−" represents minus, particularly signal subtraction. For example, the signal subtraction may be performed at each cycle by subtracting a signal value at a cycle in one signal from a signal value at a corresponding cycle in another signal.

In the mathematical equations described herein, the symbol "×" represents multiplication.

In the mathematical equations described herein, the symbol "÷" represents division.

According to the extraction of the signal for the second target nucleic acid sequence by the mathematical equation I-1, the signal detected at the relatively low detection temperature reflects a combination of the signal for the first target nucleic acid sequence and the signal for the second target nucleic acid sequence, whereas the signal detected at the relatively high detection temperature only reflects the signal for the first target nucleic acid sequence. Thus, the signal for the second target nucleic acid sequence may be obtained by subtracting the signal detected at the relatively high detection temperature from the signal detected at the relatively low detection temperature, with a proviso that the signals for the first target nucleic acid sequence at the relatively high detection temperature and the relatively low detection temperature are not changed. However, considering that the signals vary depending upon the detection temperatures, it is necessary to adjust (transform) the signal detected at the relatively high detection temperature into a signal to be expected at the relatively low detection temperature, prior to the signal subtraction. For this purpose, the first initial reference value is used.

According to an alternative embodiment, the first signal-generating means generates signals at the relatively high detection temperature and the relatively low detection temperature and the second signal-generating means generates a signal at the relatively low detection temperature, and the processing of the signal values in the step (b) is performed using the first initial reference value to extract the signal for the second target nucleic acid sequence from the signal at the relatively high detection temperature obtained in the step (a).

More particularly, the extraction of the signal for the second target nucleic acid sequence is performed by the following mathematical equation I-2:

Extracted signal for the second target nucleic acid sequence=[signal at the relatively high detection temperature obtained in the step (a)]−[(signal at the relatively low detection temperature obtained in the step (a))÷(the first initial reference value)];   <Equation I-2> wherein the first initial reference value is a ratio of the signal provided by the first signal-generating means at the relatively low detection temperature to the signal provided by the first signal-generating means at the relatively high detection temperature.

In the MuDT1 technology, the signal detected at the relatively high detection temperature may be considered as the extracted signal for the first target nucleic acid sequence because the signal for the first target nucleic acid sequence is only detected at the relatively high detection temperature.

In the mathematical equations I-1 and I-2, the first initial reference value is represented by the ratio of the signal at the relatively low detection temperature to the signal at the relatively high detection temperature. It would be understood by one of skill in the art that the signal extraction for the second target nucleic acid sequence may be accomplished with a modification using a first initial reference value represented by the ratio of the signal at the relatively high detection temperature to the signal at the relatively low detection temperature. Those of skill in the art would understand that such modification falls within the spirit and scope of the invention.

Where the present invention is applied to the MuDT2 technology, it may be performed as follows:

According to an embodiment, the two signal-generating means generate signals at the relatively high detection temperature and the relatively low detection temperature.

According to an embodiment, when the second initial reference value is greater than the first initial reference value, (i) the processing of the signal values in the step (b) is mathematically performed to extract the signal for the second target nucleic acid sequence by the first initial reference value from the signal at the relatively low detection temperature; (ii) the processing of the signal values in the step (b) is mathematically performed to extract the signal for the second target nucleic acid sequence by the first initial reference value from the signal at the relatively high detection temperature in the step (a); (iii) the processing of the signal values in the step (b) is mathematically performed to extract the signal for the first target nucleic acid sequence by the second initial reference value from the signal at the relatively low detection temperature; or (iv) the processing of the signal values in the step (b) is mathematically performed to extract the signal for the first target nucleic acid sequence by the second initial reference value from the signal the signal at the relatively high detection temperature in the step (a).

More particularly, the extraction of the signal for the second target nucleic acid sequence by the first initial reference value from signals at the relatively low detection temperature is performed by the mathematical equation I-1; the extraction of the signal for the second target nucleic acid sequence by the first initial reference value from signals at the relatively high detection temperature is performed by the following mathematical equation I-2; the extraction of the signal for the first target nucleic acid sequence by the second initial reference value from signals at the relatively low detection temperature is performed by the following mathematical equation I-3; or the extraction of the signal for the first target nucleic acid sequence by the second initial reference value from signals at the relatively high detection temperature is performed by the following mathematical equation I-4:

Extracted signal for the second target nucleic acid sequence=[signal at the relatively low detection temperature obtained in the step (a)]−[(signal at the relatively high detection temperature obtained in the step (a))×(the first initial reference value)];   <Equation I-1>

Extracted signal for the second target nucleic acid sequence=[signal at the relatively high detection temperature obtained in the step (a)]−[(signal at the relatively low detection temperature obtained in the step (a))÷(the first initial reference value)];   <Equation I-2> wherein the first initial reference value is a ratio of the signal provided by the first signal-generating means at the relatively low detection temperature to the signal provided by the first signal-generating means at the relatively high detection temperature;

Extracted signal for the first target nucleic acid sequence=[signal at the relatively low detection temperature obtained in the step (a)]−[(signal at the relatively high detection temperature obtained in the step (a))×(the second initial reference value)]; <Equation I-3>

Extracted signal for the first target nucleic acid sequence=[signal at the relatively high detection temperature obtained in the step (a)]−[(signal at the relatively low detection temperature obtained in the step (a))÷(the second initial reference value)]; <Equation I-4> wherein the second initial reference value is a ratio of the signal provided by the second signal-generating means at the relatively low detection temperature to the signal provided by the second signal-generating means at the relatively high detection temperature.

When referring to the mathematical equations I-3, each of the signals detected at the relatively low detection temperature and at the relatively high detection temperature reflects a combination of the signal for the first target nucleic acid sequence and the signal for the second target nucleic acid sequence. Assuming that the second initial reference value is greater than the first initial reference value, the multiplication of the signal at the relatively high detection temperature by the second initial reference value allows the signal for the second target nucleic acid sequence (contained in the signal detected at the relatively high detection temperature) to be transformed into the signal expected to be detected at the relatively low detection temperature. In addition, the multiplication also transforms the signal for the first target nucleic acid sequence (contained in the signal detected at the relatively high detection temperature) into the signal greater than that expected to be detected at the relatively low detection temperature. Thus, the signal subtraction of the transformed signals from the signal detected at the relatively low detection temperature will allow for the signal extraction of the first target nucleic acid sequence, since such subtraction will eliminate the signal for the second target nucleic acid sequence.

In the equations I-1, I-2, I-3 and I-4, the initial reference values are represented by the ratio of the signal at the relatively low detection temperature to the signal at the relatively high detection temperature. It would be understood by one of skill in the art that the signal extraction may be accomplished with a modification using initial reference values represented by the ratio of the signal at the relatively high detection temperature to the signal at the relatively low detection temperature. Those of skill in the art would understand that such modification falls within the spirit and scope of the invention.

It is noted that the mathematical equations I-1 and I-2 are commonly used in both the MuDT1 technology and the MuDT2 technology; whereas the mathematical equations I-3 and I-4 are used only in the MuDT2 technology. Therefore, prior to application of the mathematical equations according the method of the present invention, it is essential to ascertain which of the two technologies was carried out.

Step (c): Identification of Erroneously Extracted Signal and Application of Amended Reference Value (S130, S140)

The extracted signal is analyzed to identify whether the extracted signal satisfies a predetermined accuracy criterion; when the extracted signal does not satisfy the accuracy criterion, the step (b) is repeated using an amended reference value instead of the initial reference value to re-extract the signal for the first target nucleic acid sequence or the second target nucleic acid sequence.

In the step (c), the signal extracted in the step (b) is analyzed to identify whether it is correctly (or suitably, normally, accurately) extracted. When the signal extraction is identified to be incorrect (or unsuitable, abnormal, erroneous, inaccurate), the initial reference value is determined to be unsuitable and an amended reference value instead of the initial reference value is applied for signal re-extraction. In this regard, the step (c) may comprise the substeps of: (c-1) identifying whether the extracted signal is correctly or suitably extracted; and (c-2) re-extracting a signal by using an amended reference value instead of the initial reference value with a proviso that the extracted signal is identified to be incorrect or unsuitable.

Substep (c-1): Identification of Correctness of Signal Extraction

In the substep of (c-1), the signal extracted in the step (b) is analyzed to identify whether it is correctly or suitably extracted. The identification may be done by analyzing whether the extracted signal shows a theoretically-predicted signal pattern. Where the extracted signal shows a theoretically-predicted signal pattern, it is identified to be correctly (or normally) extracted for a target nucleic acid sequence. In contrast, where the extracted signal shows no theoretically-predicted signal pattern, it is identified not to be correctly (or normally) extracted. Such signal pattern analysis may be performed manually or automatically.

When a target nucleic acid sequence is present in a sample, a theoretically-predicted signal pattern for the target nucleic acid sequence will be an increasing or growing pattern (otherwise, a decreasing pattern); whereas, when a target nucleic acid sequence is absent in a sample, a theoretically-predicted signal pattern for the target nucleic acid sequence will be substantially zero (0) value (e.g., RFU 0)-approaching pattern.

Whether the signal is correctly or suitably extracted is identified using an accuracy criterion.

The term used herein "accuracy criterion" with reference to signal extraction means a criterion allowing for differentially discriminating correctly (accurately) extracted signals from erroneously extracted signals. For example, the accuracy criterion may mean a criterion allowing for identifying whether the extracted signal shows a theoretically-predicted signal pattern. The accuracy criterion may mean a criterion for determining suitability (accuracy) of the initial reference value for signal extraction.

The accuracy criterion may be suitably predetermined by one of skill in the art, as long as it can distinguish correctly extracted signals from erroneously extracted signals. The accuracy criterion may be, without limitation, any condition or value. The accuracy criterion may be empirically predetermined.

In an embodiment, the accuracy criterion may be predetermined in consideration of the pattern of signals to be theoretically predicted in signal extraction.

As indicated above, the accuracy of signal extraction is based on whether the extracted signal satisfies the accuracy criterion.

In other words, the identification that the extracted signal satisfies the accuracy criterion demonstrates suitability of the initial reference value for signal extraction, whereas the identification that the extracted signal does not satisfy the accuracy criterion demonstrates unsuitability of the initial reference value for signal extraction.

Given that the initial reference value used in the step (b) is suitable, the extracted signal is very likely to show a theoretically-predicted signal pattern. For example, assumed that the initial reference value is suitable and normal signals show positive values (e.g., increasing or growing pattern) or substantially zero (0) value (e.g., RFU 0)-approaching pattern (e.g., background pattern), it can be determined that signals showing negative values (e.g. decreasing pattern) are erroneous. Where an accuracy criterion for elevating accuracy of such determination is applied by adopting a threshold as any value of less than zero (0) and the extracted signal has a signal value crossing the threshold, the extracted signal can be determined to be erroneous. In contrast, where signals showing positive values (e.g. increasing or growing pattern) are theoretically erroneous and a threshold is adopted as any value of more than zero (0), the extracted signal having a signal value crossing the threshold can be determined to be erroneous.

The accuracy criterion may be exemplified by a predetermined threshold.

In an embodiment of the present invention, the accuracy criterion is that the extracted signal has no signal value crossing a predetermined threshold (or a predetermined threshold line).

For example, where the accuracy criterion is that the extracted signal has no signal value crossing a predetermined threshold, the application of the amended reference value is not required so long as the extracted signal has no signal value crossing a predetermined threshold. In other words, where the extracted signal has no signal value crossing a predetermined threshold, the amended reference value need not to be determined and procedures of the present method are terminated. In such case, the signal extracted by using the initial reference value is regarded as an accurately extracted signal.

The accuracy criterion represented by the extracted signal having no signal value crossing a predetermined threshold encompasses two cases: the extracted signal having signal values of more than a predetermined threshold and the extracted signal having signal values of less than a predetermined threshold.

The term "the extracted signal having signal value of more than a predetermined threshold" means that the signal values at all cycles in the extracted signal exceed a predetermined threshold. Likewise, the term "the extracted signal having signal values of less than a predetermined threshold" means that the signal values at all cycles in the extracted signal fall below a predetermined threshold.

For example, where the accuracy criterion is that the extracted signal has signal values of more than the predetermined threshold and the extracted signal is determined to have signal values of more than the predetermined threshold, the signal does not need to be re-extracted with the amended reference value. Where the accuracy criterion is that the extracted signal has signal values of less than the predetermined threshold and the extracted signal is determined to have signal values less than the predetermined threshold, the signal does not need to be re-extracted with the amended reference value.

The threshold may be predetermined based on the theoretically predicted signal pattern, upon extraction of signal according to the present invention.

As one example, where a theoretically predicted normal signal pattern is positive values (e.g., increasing or growing pattern) or substantially zero (0) value (e.g., RFU 0)-approaching pattern (e.g., a background pattern), the threshold may be any suitable negative value and the accuracy criterion may be that the extracted signal has signal values of more than the threshold. For example, the threshold may be, e.g., RFU −10, −20, −30, −40, −50, −60, −70, −80, −90, −100, −200, −300 or less. In this case, the extracted signal having signal values of not more than the threshold, i.e., the extracted signal having a signal value crossing the threshold, can be regarded as an abnormally extracted signal.

As another example, where a theoretically predicted normal signal pattern is negative values (e.g., decreasing pattern) or substantially zero (0) value (e.g., RFU 0)-approaching pattern (e.g., a background pattern), the threshold may be any suitable positive value and the accuracy criterion may be that the extracted signal has signal values of less than the threshold. For example, the threshold may be, e.g., RFU 10, 20, 30, 40, 50, 60, 70, 80, 90, 100, 200, 300 or more, but not limited thereto. In this case, the extracted signal having signal values of not less than the threshold, i.e., the extracted signal having a signal value crossing the threshold, can be regarded as an abnormally extracted signal.

The threshold should be appropriately selected not to avoid any misinterpretation of normally extracted signal into erroneously extracted signal, e.g., due to signal noises or fluctuations.

Substep (c-2): Re-Extraction of Signal by Amended Reference Value

In the substep of (c-2), an amended reference value is applied with a proviso that the extracted signal does not satisfy the accuracy criterion.

According to the present invention, when the extracted signal does not satisfy the accuracy criterion, an amended reference value is newly obtained and a signal for a corresponding target nucleic acid sequence is re-extracted (i.e., the step (b) is re-performed).

The term "re-extracted," "re-extracting," or "re-extraction" in the context of the signal refers to that the previously extracted signal is discarded and newly extracted signal is obtained.

The amended reference value is another reference value other than the initial reference value, which is used for accurate signal extraction.

The amended reference value may be determined in various fashions, as will be described below.

According to an embodiment, the amended reference value is determined such that the re-extracted signal, satisfies the accuracy criterion. In other words, the amended reference value is selected among the values rendering the extracted signal to satisfy the accuracy criterion.

According to an embodiment, when the accuracy criterion is that the extracted signal does not cross a predetermined threshold (and the extracted signal crosses the predetermined threshold), the amended reference value is determined such that the re-extracted signal does not cross the predetermined threshold. In other words, the amended reference value is selected among the values rendering the extracted signal not to cross the predetermined threshold.

According to an embodiment, when the accuracy criterion is that the extracted signal has a signal value of more than a predetermined threshold (and the extracted signal has a signal value of not more than a predetermined threshold), the amended reference value is determined such that the re-extracted signal has a signal value of more than the predetermined threshold. In other words, the amended reference value is selected among the values rendering the extracted signal to have a signal value of more than the predetermined threshold. In such case, the amended reference value is determined as a value lower than the initial reference value.

According to an embodiment, when the accuracy criterion is that the extracted signal has a signal value of less than a predetermined threshold (and the extracted signal has a signal value of not less than a predetermined threshold), the amended reference value is determined such that the re-extracted signal has a signal value of less than the predetermined threshold. In other words, the amended reference value is selected among the values rendering the extracted signal to have a signal value of less than the predetermined threshold. In such case, the amended reference value is determined as a value higher than the initial reference value.

According to an embodiment, the amended reference value is determined by increasing or decreasing the initial reference value with a value interval until the re-extracted signal satisfies the accuracy criterion. Where the extracted signal has a signal value crossing a threshold of less than 0, amended reference values less than the initial reference value may be selected in a decreasing manner and applied until the re-extracted signal does not cross the threshold. Where the extracted signal has a signal value crossing a threshold of more than 0, amended reference values more than the initial reference value may be selected in an increasing manner and applied until the re-extracted signal does not cross the threshold.

For example, where the initial reference value is "2.00" and the extracted signal has a signal value crossing a threshold of less than 0, an amended reference value smaller than the initial reference value, e.g., 1.90 is selected and the signal is then re-extracted by using the amended reference value. If the re-extracted signal still has a signal value crossing the threshold, another amended reference value smaller than 1.90, e.g., 1.80 is selected and the signal is then re-extracted by using the amended reference value. This process is repeated until the re-extracted signal has no signal value crossing the threshold. If the re-extracted signal has no signal value crossing the threshold, the process is terminated. Then, the amended reference value finally employed and the signal extracted using the same are adopted as a suitable reference value and a correctly extracted signal for a target nucleic acid sequence. The value interval used for selection of amended reference value may or may not be constant. For example, when the initial reference value is "2.00", the amended reference values subsequently selected may be "1.90", "1.80", "1.70" . . . or "1.90", "1.70", "1.30" . . . etc. (with a fixed interval).

Alternatively, when the initial reference value is "2.00", the amended reference values subsequently selected may be "1.92", "1.70", "1.45" etc. (with an unfixed interval).

The amended reference value as described above may be applied to all cycles of the signals in the step (a) instead of the initial reference value to re-extract the signal for the first target nucleic acid sequence or the second target nucleic acid sequence.

According to another embodiment, the amended reference value may be determined by the relationship of change in signals between the signals detected at the relatively high detection temperature and the relatively low detection temperature obtained in the step (a). The amended reference value may be a ratio between the signals detected at the relatively high detection temperature and the relatively low detection temperature obtained in the step (a).

In a particular embodiment, the amended reference value may be determined in accordance with the following mathematical equation IV:

Amended Reference value for a target=[signal at the relatively low detection temperature for a sample being analyzed]÷[signal at the relatively high detection temperature for a sample being analyzed] <Equation IV>

Particularly, the amended reference value is determined by applying a predetermined threshold as the accuracy criterion to the extracted signal, identifying a point at which the extracted signal firstly crosses the predetermined threshold, selecting a cycle at or after the identified point, and calculating at the selected cycle the relationship of change in signals at the relatively high detection temperature and the relatively low detection temperature in the step (a). The amended reference value has to be calculated in a same manner with the initial reference value. For example, when the initial reference value is calculated by the ratio of the signal at the relatively low detection temperature to the signal at the relatively high detection temperature, the amended reference value has to be calculated by the ratio of the signal at the relatively low detection temperature to the signal at the relatively high detection temperature. The relationship of change in signals calculated at the selected cycle may be used for a fixed amended-reference value approach described below.

According to an embodiment, the selected cycle may be any cycle having the signal value above or below the predetermined threshold. For example, where the accuracy criterion is that the extracted signal has signal values more than the predetermined threshold, the selected cycle may be any cycle having the signal value below the predetermined threshold. On the other hand, where the accuracy criterion is that the extracted signal has signal values less than the predetermined threshold, the selected cycle may be any cycle having the signal value above the predetermined threshold.

According to an embodiment, the selected cycle may be a cycle having the highest or lowest signal value. For example, where the accuracy criterion is that the extracted signal has signal values more than the predetermined threshold, the selected cycle is a cycle having the lowest (minimum) signal value. On the other hand, where the accuracy criterion is that the extracted signal has signal values less than the predetermined threshold, the selected cycle is a cycle having the highest (maximum) signal value.

According to an embodiment, the amended reference value is a value for rendering the signal value at the selected cycle to be higher than or to be lower than the predetermined threshold, or to a background level. The term "background level" refers to signal values to be detected when a target is not significantly amplified, e.g., around RFU 0.

According to an embodiment, the amended reference value is determined by applying a predetermined threshold as the accuracy criterion to the extracted signal, identifying a point at which a signal value firstly crosses the predetermined threshold, selecting a cycle at or after the identified point, and calculating at the selected cycle the relationship of change in signals at the relatively high detection temperature and the relatively low detection temperature in the step (a); and a plurality of additional amended reference values are determined by calculating at the cycles before the selected cycle the relationship of change in signals at the relatively high detection temperature and the relatively low detection temperature in the step (a). In such case, the selected cycle is a cycle having the highest or lowest signal value. The relationship of change in signals calculated at the selected cycle may be used for a variable amended-reference value approach described below.

In the aforementioned embodiment, the amended reference value is applied to the selected cycle of the signals in the step (a) and all cycles after the selected cycle of the signals in the step (a); and each of the additional amended reference values is applied to each cycle before the selected cycle of the signals in the step (a) instead of the initial reference value to re-extract the signal for the first target nucleic acid sequence or the second target nucleic acid sequence.

Where the present invention is applied to the MuDT1 technology, it may be embodied as follows:

According to an embodiment, the first signal-generating means generates signals at the relatively high detection temperature and the relatively low detection temperature and the second signal-generating means generates a signal at the relatively low detection temperature, and the processing of the signal values in the step (b) is mathematically performed by using the first initial reference value to extract the signal for the second target nucleic acid sequence from the signals at the relatively low detection temperature obtained in the step (a), and the accuracy criterion is that the extracted signal has a signal value of more than a predetermined threshold.

According to an embodiment, the extraction of the signal for the second target nucleic acid sequence may be performed by the mathematical equation I-1.

According to an embodiment, when the extracted signal for the second target nucleic acid sequence has a signal value of not more than the predetermined threshold, the step (b) is repeated using an amended reference value instead of the initial reference value to re-extract the signal for the second target nucleic acid sequence; wherein the amended reference value is determined such that re-extracted signal has a signal value of more than the predetermined threshold.

The amended reference value may be determined such that a signal value at any cycle among cycles having signal values (extracted by the first initial reference value) not more than the predetermined threshold is rendered to be higher than the predetermined threshold or to be a background level (particularly, a background level). According to an embodiment, the amended reference value may be determined such that the signal value not more than the predetermined threshold is rendered to be between the predetermined threshold and the background level.

More particularly, the amended reference value is determined such that a signal value at a cycle having the lowest signal value among values of the signal extracted by the first initial reference value is rendered to be higher than the predetermined threshold or to be a background level (particularly, a background level). According to an embodiment, the amended reference value may be determined such that the lowest signal value is rendered to be between the predetermined threshold and the background level.

Where the first initial reference value is considered to be suitable, a signal for the second target nucleic acid sequence extracted should have theoretically positive values and be around RFU 0 value in the presence and absence of the second target nucleic acid sequence, respectively. However, where a signal for the second target nucleic acid sequence extracted by any particular reference value shows negative values, it is considered to be erroneous, addressing that the initial reference value has to be amended. For better accuracy of such determination, a threshold having a suitable value less than 0 as an accuracy criterion (e.g., threshold) is applied in such a manner that the extracted signal not more than the threshold is considered to be erroneous and then amended reference value is applied.

Alternatively, the first signal-generating means generates signals at the relatively high detection temperature and the relatively low detection temperature and the second signal-generating means generates a signal at the relatively low detection temperature, and the processing of the signal values in the step (b) is performed using the first initial reference value to extract the signal for the second target nucleic acid sequence from the signal at the relatively high detection temperature obtained in the step (a), and the accuracy criterion is that the extracted signal has a signal value of less than a predetermined threshold.

According to an embodiment, the extraction of the signal for the second target nucleic acid sequence may be performed by the mathematical equation I-2.

According to an embodiment, when the extracted signal for the second target nucleic acid sequence has a signal value of not less than the predetermined threshold, the step (b) is repeated using the amended reference value instead of the initial reference value to re-extract the signal for the second target nucleic acid sequence; wherein the amended reference value is determined such that re-extracted signal has a signal value of less than the predetermined threshold The amended reference value may be determined such that a signal value at any cycle among cycles having signal values (extracted by the first initial reference value) not less than the predetermined threshold is rendered to be lower than the predetermined threshold or to be a background level (particularly, a background level). According to an embodiment, the amended reference value may be determined such that the signal value not less than the predetermined threshold is rendered to be between the predetermined threshold and the background level.

More particularly, the amended reference value is determined such that a signal value at a cycle having the highest signal value among values of the signal extracted by the first initial reference value is rendered to be lower than the predetermined threshold or to be a background level. According to an embodiment, the amended reference value may be determined such that the highest signal value is rendered to be between the predetermined threshold and the background level.

Where the first initial reference value is considered to be suitable, a signal for the second target nucleic acid sequence extracted should have theoretically negative values and be around RFU 0 value in the presence and absence of the second target nucleic acid sequence, respectively. However, where a signal for the second target nucleic acid sequence extracted by any particular reference value shows positive values, it is considered to be erroneous, addressing that the initial reference value has to be amended. For better accuracy of such determination, a threshold having a suitable value more than 0 as an accuracy criterion (e.g., threshold) is applied in such a manner that the extracted signal not less than the threshold is considered to be erroneous and then amended reference value is applied.

The determination and application of the amended reference value may be performed in two alternative fashions: (i) Fixed amended-reference value approach; and (ii) Variable amended-reference value approach.

Particularly, the amended reference value is obtained by using signals generated and detected by incubation of the sample with the two signal-generating means, which is distinctly different from the initial reference value obtained by using a standard material.

Figure 4A:
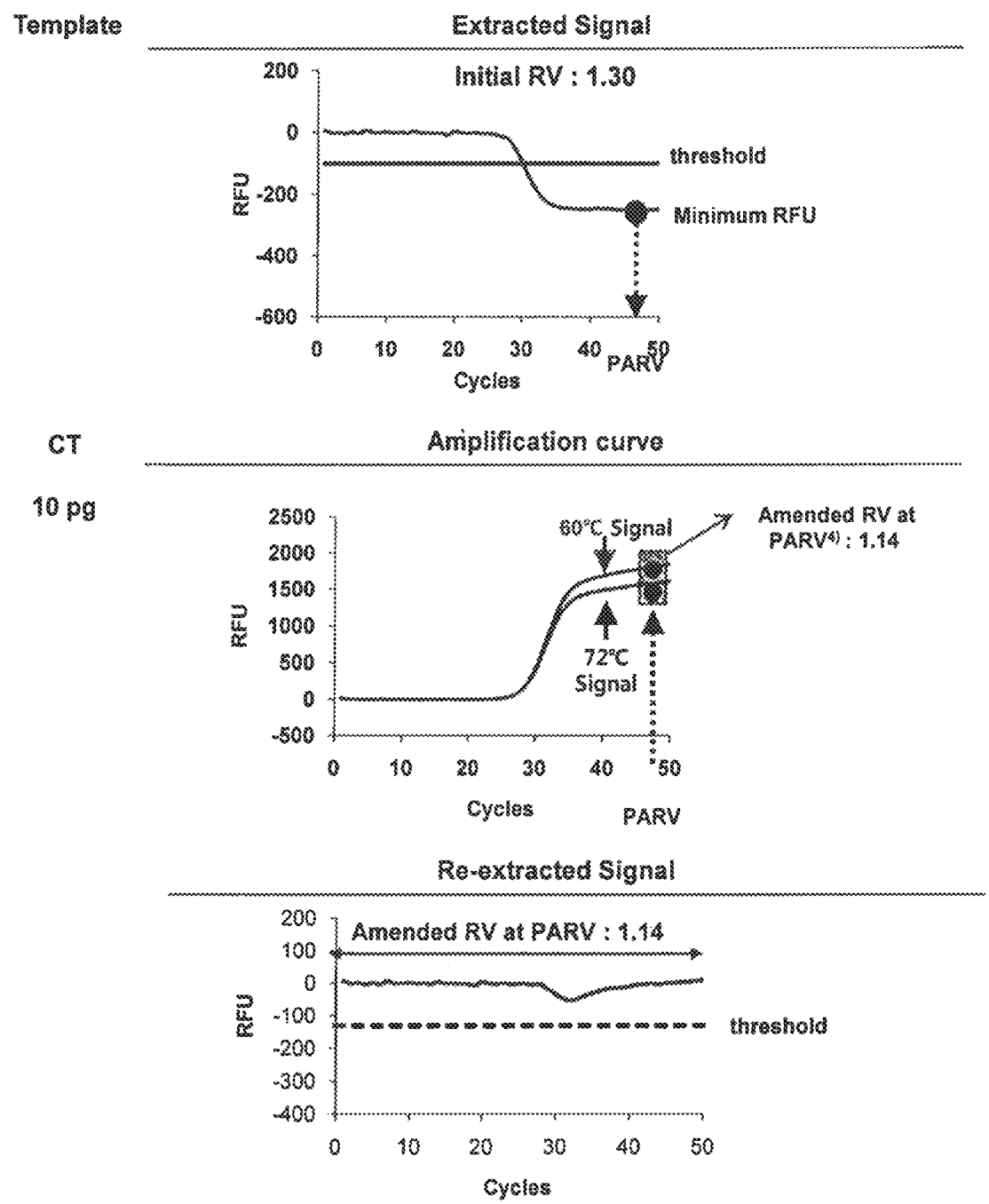
FIG. 4A represents an embodiment of the fixed amended-reference value approach for obtaining a re-extracted signal. The extracted signal in FIG. 3 was evaluated whether it satisfied the accuracy criterion (the upper part), an amended reference value was obtained at the selected PARV (the middle part) and a signal re-extraction was performed by using the amended reference value (the lower part). In the figure, 'Initial RV' represents the initial reference value for CT; 'threshold' represents the threshold for determining the suitability of the RV from extracted signals; 'PARV' represents the point for setting an amended reference value; and 'Amended RV at PARV' represents the amended reference value for CT calculated by the signals at PARV.

The fixed amended-reference value approach is exemplified in FIG. 4A.

As illustrated in FIG. 4A, the fixed amended-reference value may be determined by applying a predetermined threshold as the accuracy criterion to the extracted signal of the step (b), identifying a point at which a signal value firstly crosses the predetermined threshold, selecting a cycle at or after the identified point, and calculating at the selected cycle the relationship of change in signals at the relatively high detection temperature and the relatively low detection temperature in the step (a).

The predetermined threshold represents a threshold for determining the suitability of the initial reference value used for signal extraction. If the extracted signal crosses the predetermined threshold, the signal is regarded as an erroneously extracted signal, addressing that the initial reference value has to be amended. Afterwards, a point at which the extracted signal firstly crosses the predetermined threshold is identified. Subsequently, a particular cycle at or after the identified point is selected for calculation of amended reference value. The selected cycle is named as PARV (point for setting amended reference value). In an embodiment, the PARV may be a cycle having the lowest or highest signal value depending on the predetermined threshold applied to the extracted signal of the step (b). For example, where the predetermined threshold applied to the extracted signal of the step (b) is a positive value, the PARV may be a cycle having the highest signal value. Where the predetermined threshold applied to the extracted signal of the step (b) is a negative value, the PARV may be a cycle having the lowest signal value.

In the fixed amended-reference value approach, only one amended reference value, which is calculated at the selected cycle, i.e., PARV is used for signal re-extraction.

In the fixed amended-reference value approach, the amended reference value calculated by PARV is applied to all cycles of the signals in the step (a) instead of the initial reference value to re-extract the signal for the first target nucleic acid sequence or the second target nucleic acid sequence.

The application of the amended reference value to all cycles the signals in the step (a) means that the amended reference value is used for a mathematical processing of the signal values at all cycles of the signals detected at the relatively high detection temperature and at the relatively low detection temperature in the step (a).

In the fixed amended-reference value approach, the amended reference value calculated at PARV may be applied to all cycles of the signals in the step (a) to re-extract the signal for the second target nucleic acid sequence by using the following mathematical equation II-1 or II-2:

Re-extracted signal for the second target nucleic acid sequence=[signal at the relatively low detection temperature obtained in the step (a)]−[(signal at the relatively high detection temperature obtained in the step (a))×(the first amended reference value)];  <Equation II-1>

Re-extracted signal for the second target nucleic acid sequence=[signal at the relatively high detection temperature obtained in the step (a)]−[(signal at the relatively low detection temperature obtained in the step (a))÷(the first amended reference value)];  <Equation II-2> wherein the first amended reference value is a ratio of the signal at the relatively low detection temperature obtained in the step (a) to the signal at the relatively high detection temperature obtained in the step (a).

Upon applying the first amended reference value, the Equation II-1 is used instead of the Equation I-1, and the Equation II-2 is used instead of the Equation I-2.

The variable amended-reference value approach is exemplified in FIG. 5A.

Unlike the fixed amended-reference value approach, the variable amended-reference value approach further employs additional amended reference values. More particularly, one amended reference value is applied to cycles ranging from PARV to an end cycle; and a plurality of additional amended reference values are applied to cycles ranging from a start cycle to PARV.

According to the variable amended-reference value approach, the amended reference value is determined by applying a predetermined threshold as the accuracy criterion to the extracted signal, identifying a point at which a signal value firstly crosses the predetermined threshold, selecting a cycle at or after the identified point, and calculating at the selected cycle the relationship of change in signals at the relatively high detection temperature and the relatively low detection temperature in the step (a); and a plurality of additional amended reference values are determined by calculating at the cycles before the selected cycle the relationship of change in signals at the relatively high detection temperature and the relatively low detection temperature in the step (a).

In the variable amended-reference value approach, the selected cycle is a cycle having the highest or lowest signal value.

As illustrated in FIG. 5A, the PARV is determined and the amended reference value at the PARV is calculated in the same manner as the fixed amended-reference value approach.

The amended reference value is applied to the selected cycle of the signals in the step (a) and all cycles after the selected cycle of the signals in the step (a); and each of the additional amended reference values is applied to each cycle before the selected cycle of the signals in the step (a) instead of the initial reference value to re-extract the signal for the first target nucleic acid sequence or the second target nucleic acid sequence.

The amended reference value at the PARV is applied to the PARV and all cycles after the PARV (i.e., from a cycle immediately after the PARV to an end cycle) for re-extraction of the target signal. For example, when PARV is $35^{th}$ cycle and the amended reference value calculated at the $35^{th}$ cycle is 1.30, 1.30 is applied to the $35^{th}$ cycle and all cycles following the $35^{th}$ cycle (e.g., from $36^{th}$ cycle to an end cycle) to re-extract the target signal. Meanwhile, additional amended reference values are calculated at each cycle before the PARV. The additional reference values are each applied to corresponding cycles before the PARV. For example, when PARV is $35^{th}$ cycle, additional amended reference values are calculated at each of cycles ranging from $1^{st}$ cycle to $34^{th}$ cycle and are applied to corresponding cycles ranging from $1^{st}$ cycle to $34^{th}$ cycle for signal re-extraction. Where signal re-extraction by application of the additional amended reference values is performed for cycles before the PARV, the signal values re-extracted at the cycles are rendered to be a background level (e.g., zero (0) value; RFU 0). In other words, the variable amended-reference value approach considers signal values at cycles before the PARV to be a background signal and adjusts those to be a background level (e.g., zero (0) value). FIG. 5A illustrates an embodiment in which the additional amended reference values are calculated at cycles before the PARV and then applied. Alternatively, in considering that signal values at cycles before the PARV in the re-extracted signal are adjusted to be a background level (e.g., zero (0) value) by application of the additional amended reference values, signal values at cycles before the PARV in the re-extracted signal may be arbitrarily altered to be a background level (e.g., zero (0) value) with no calculation of the additional amended reference values. Alternatively, signal values at cycles before PARV in the re-extracted signal may be arbitrarily altered to be a same value as a signal value at PARV in the re-extracted signal.

In particular, the PARV is a cycle having the lowest or highest signal value depending on the predetermined threshold applied to the extracted signal of the step (b). For example, where the predetermined threshold applied to the extracted signal of the step (b) is a positive value, the PARV may be a cycle having the highest signal value. Where the predetermined threshold applied to the extracted signal of the step (b) is a negative value, the PARV may be a cycle having the lowest signal value.

Further, the PARV is a cycle having the lowest or highest signal value depending on the pattern of signals erroneously extracted. For example, when the erroneously extracted signals have a decreasing pattern, the PARV may be a cycle having the lowest signal value. When the erroneously extracted signals have an increasing pattern, the PARV may be a cycle having the highest signal value.

In the variable amended-reference value approach, the amended reference value is applied to the PARV and all cycles after a cycle having the highest or lowest signal value of the signals obtained in the step (a), each additional amended reference value for rendering signal values of cycles to be a background level is applied to each cycle before the highest or lowest signal valued cycle.

In the variable amended-reference value approach, if a cycle having the highest or lowest signal value, i.e., PARV, is an end cycle, there is no cycle after the PARV. In this case, the application of each additional amended reference value to each of all cycles is only required.

As described above, while the fixed amended-reference value approach calculates an amended reference value at a certain cycle (e.g., PARV) and then applies it to all cycles, the variable amended-reference value approach calculates not only an amended reference value at a certain cycle (e.g., PARV) for application to all cycles after the cycle but also additional amended reference value for application to cycles before the cycle.

Where the present invention is applied to the MuDT2 technology, it may be embodied as follows:

According to an embodiment, the two signal-generating means generate signals at the relatively high detection temperature and the relatively low detection temperature, and the accuracy criterion is that the extracted signal has a signal value of more than or less than a threshold. The accuracy criterion may be varied depending on theoretically-predicted signal patterns corresponding to correctly extracted signals. Where the theoretically-predicted signal pattern in a correctly extracted signal is a positive pattern (e.g. increasing pattern), the accuracy criterion may be that the extracted signal has a signal value of more than a threshold. Where the theoretically-predicted signal pattern corresponding to correctly extracted signals is a negative pattern (e.g. decreasing pattern), the accuracy criterion may be that the extracted signal has a signal value of less than a threshold.

More particularly, when the second initial reference value is greater than the first initial reference value, (i) the processing of the signal values in the step (b) is mathematically performed to extract the signal for the second target nucleic acid sequence by the first initial reference value from the signal at the relatively low detection temperature; (ii) the processing of the signal values in the step (b) is mathematically performed to extract the signal for the second target nucleic acid sequence by the first initial reference value from the signal at the relatively high detection temperature in the step (a); (iii) the processing of the signal values in the step (b) is mathematically performed to extract the signal for the first target nucleic acid sequence by the second initial reference value from the signal at the relatively low detection temperature; or (iv) the processing of the signal values in the step (b) is mathematically performed to extract the signal for the first target nucleic acid sequence by the second initial reference value from the signal the signal at the relatively high detection temperature in the step (a); and when the mathematical processing is performed according to (i), the accuracy criterion is that the extracted signal has a signal value of more than the threshold; wherein when the mathematical processing is performed according to (ii), the accuracy criterion is that the extracted signal has a signal value of less than the threshold; wherein when the mathematical processing is performed according to (iii), the accuracy criterion is that the extracted signal has a signal value of less than the threshold; or wherein when the mathematical processing is performed according to (iv), the accuracy criterion is that the extracted signal has a signal value of more than the threshold.

Much more particularly, when the accuracy criterion is that the extracted signal has a signal value of more than the threshold and the extracted signal has a signal value of not more than the threshold, the step (b) is repeated using the amended reference value for rendering the signal value to be more than the threshold; and when the accuracy criterion is that the extracted signal has a signal value of less than the threshold and the extracted signal has a signal value of not less than the threshold, the step (b) is repeated using the amended reference value for rendering the signal value to be less than the threshold.

Where a signal for the second target nucleic acid sequence is extracted from signals at the relatively low detection temperature and the first initial reference value is suitable, the signal for the second target nucleic acid sequence extracted as described above should be theoretically positive or around zero (0) value. However, where the signal for the second target nucleic acid sequence extracted by any particular reference value has a negative value, it may be evaluated as erroneous signal.

Where a signal for the second target nucleic acid sequence is extracted from signals at the relatively high detection temperature and the first initial reference value is suitable, the signal for the second target nucleic acid sequence extracted as described above should be theoretically negative or around zero (0) value. However, where the signal for the second target nucleic acid sequence extracted by any particular reference value has a positive value, it may be evaluated as erroneous signal.

Where a signal for the first target nucleic acid sequence is extracted from signals at the relatively low detection temperature and the second initial reference value is suitable, the signal for the first target nucleic acid sequence extracted as described above should be theoretically negative or around zero (0) value. However, where the signal for the first target nucleic acid sequence extracted by any particular reference value has a positive value, it may be evaluated as erroneous signal.

Where a signal for the first target nucleic acid sequence from signals at the relatively high detection temperature is extracted and the second initial reference value is suitable, the signal for the first target nucleic acid sequence extracted as described above should be theoretically positive or around zero (0) value. However, where the signal for the first target nucleic acid sequence extracted by any particular reference value has a negative value, it may be evaluated as erroneous signal.

According to an embodiment, when the accuracy criterion is that the extracted signal has a signal value of more than the threshold and the extracted signal has a signal value of not more than the threshold, and the step (b) is repeated using the amended reference value for rendering the signal value to be more than the threshold, the amended reference value is determined such that a signal value at a cycle having the lowest signal value among values of the signal extracted is rendered to be higher than the predetermined threshold or to be a background level.

According to an embodiment, when the accuracy criterion is that the extracted signal has a signal value of less than the threshold and the extracted signal has a signal value of not less than the threshold, and the step (b) is repeated using the amended reference value for rendering the signal value to be less than the threshold, the amended reference value is determined such that a signal value at a cycle having the highest signal value among values of the signal extracted is rendered to be lower than the predetermined threshold or to be a background level.

The application of the amended reference value may be performed in a similar manner to that for the MuDT1 technology. For instance, where the signal for the second target nucleic acid sequence is performed by Equation I-1 or I-2, the application of the amended reference value may be applied to all cycles of the signals in the step (a) to correctly re-extract the signal for the second target nucleic acid sequence by using Equation II-1 or II-2. Where the signal for the first target nucleic acid sequence is performed by Equation I-3 or I-4, the application of the amended reference value may be applied to all cycles of the signals in the step (a) to correctly re-extract the signal for the second target nucleic acid sequence by using the following Equation II-3 or II-4:

Re-extracted signal for the first target nucleic acid sequence=[signal at the relatively low detection temperature obtained in the step (a)]−[(signal at the relatively high detection temperature obtained in the step (a))×(the second amended reference value)]  <Equation II-3>

Re-extracted signal for the first target nucleic acid sequence=[signal at the relatively high detection temperature obtained in the step (a)]−[(signal at the relatively low detection temperature obtained in the step (a))÷(the second amended reference value)]  <Equation II-4> wherein the second amended reference value is a ratio of the signal at the relatively low detection temperature obtained in the step (a) to the signal at the relatively high detection temperature obtained in the step (a).

In the fixed amended-reference value approach, the amended reference value may be applied to all cycles of the signals in the step (a) to correctly re-extract the signal for the second target nucleic acid sequence by using the mathematical equation II-1, II-2, II-3 or II-4. In the approach, the amended reference value may be a ratio of the signals obtained in step (a).

In the variable amended-reference value approach, the amended reference value is applied to a cycle having the highest or lowest signal value of the signals obtained in the step (a) and all cycles after that cycle, and each additional amended reference value for rendering signal values of cycles to be a background level is applied to each cycle before the highest or lowest signal valued cycle. In the approach, the amended reference value may be a ratio of the signals obtained in step (a). Further, the additional amended reference value may be also a ratio of the signals obtained in step (a).

The details for the additional amended reference value may be described with reference to descriptions described above.

The extracted (or re-extracted) signal for a target nucleic acid sequence by the present invention comprises no signals from the other target nucleic acid sequence. The extracted (or re-extracted) signal represents not only signals of an amplification curve of the target nucleic acid sequence but also other-shaped signals having other information.

For example, in an embodiment using the MuDT1 technology, where the signal extraction is performed by subtraction of signals at the relatively low detection temperature by signals at the relatively high detection temperature, its result may represent signals (positive-patterned signals) of an amplification curve of the target nucleic acid sequence. Where the signal extraction is performed by subtraction of signals at the relatively high detection temperature by signals at the relatively low detection temperature, its result may represent signals (positive-patterned signals) different from those of the amplification curve.

In an embodiment using the MuDT2 technology, the extracted (or re-extracted) signal may represent an altered curve for target detection other than an amplification curve.

The signal extraction can be considered as extraction of signals for the target nucleic acid sequence in the senses that the extracted signal comprises signals from only target nucleic acid sequence with no signals from the other target nucleic acid sequence.

In the mathematical equations I-1, I-2, I-3 and I-4, the first initial reference value is represented by the ratio of the signal at the relatively low detection temperature to the signal at; the relatively high detection temperature. It would be understood by one of skill in the art that the signal extraction for the second target nucleic acid sequence may be accomplished with a little modification using a first initial reference value represented by the ratio of the signal at the relatively high detection temperature to the signal at the relatively low detection temperature. Those of skill in the art would understand that such modification falls within the spirit and scope of the invention.

According to the MuDT1 technology and the MuDT2 technology, a signal for a target nucleic acid sequence can be extracted from signals for three or more target nucleic acid sequences by using a reference value, in a similar manner to the aforementioned method. In such cases, the extracted signal may exhibit erroneous signal patterns, and thus the inventive method can be also applied to correctly re-extract the signal. When the extracted signal shows erroneous signal pattern (i.e., when the extracted signal does not satisfy a predetermined threshold), the re-extraction of signal can be performed by using an amended reference value instead of an initial reference value.

In an embodiment for extracting a signal for a target nucleic acid sequence from signals for two target nucleic acid sequences in a sample, the two target nucleic acid sequences in the sample are those selected among three or more target nucleic acid sequences in the sample.

The present method can be involved in extraction of a signal for a target nucleic acid sequence in a reaction capable of generating three or more signals for three or more target nucleic acid sequences.

Furthermore, the signal extraction for three target nucleic acid sequences may be performed in a similar way to the signal extraction for two target nucleic acid sequences.

In other words, the signal extraction for a target nucleic acid sequence from signals for three or more target nucleic acid sequences in a sample may comprise an aspect of signal extraction for a target nucleic acid sequence from signals for two target nucleic acid sequences in a sample.

As an example, a method for extracting a signal for a target nucleic acid sequence from signals for three target nucleic acid sequences in a sample is described in detail.

According to the MuDT1 technology, three signal-generating means (e.g., a first signal-generating means, a second signal-generating means and a third signal-generating means) and three detection temperature (e.g., a relatively high detection temperature, a relatively median detection temperature and a relatively low detection temperature) are employed.

The first signal-generating means generates signals at the relatively high detection temperature, the relatively median detection temperature and the relatively low detection temperature; the second signal-generating means generates signals at the relatively median detection temperature and the relatively low detection temperature; and the third signal-generating means generate signal at the relatively low detection temperature.

The sample is incubated with a first signal-generating means capable of generating a signal for a first target nucleic acid sequence, a second signal-generating means capable of generating a signal for a second target nucleic acid sequence, and a third signal-generating means capable of generating a signal for a second target nucleic acid sequence in a single reaction vessel and detecting signals at a relatively high detection temperature, a relatively median detection temperature and a relatively low detection temperature by the single type of detector. Afterwards, the signal detected at the relatively high detection temperature and the signal detected at the relatively median detection temperature are mathematically processed by using a first initial reference value to extract the signal for the second target nucleic acid sequence; wherein the first initial reference value is a value representing a relationship of change in signals provided by the first signal-generating means at the relatively high detection temperature and the relatively median detection temperature. The suitability of the first initial reference value is verified and corrected by the present method.

Then, if it is determined that one of the first target nucleic acid sequence and the second target nucleic acid sequence is absent from a result of the above extraction step, a signal extraction from the signals detected at the relatively low detection temperature and the signal detected at the relatively median detection temperature can be performed according to the present method as if there may be two target nucleic acid sequences in the sample.

Meanwhile, if it is determined that both of the first target nucleic acid sequence and the second target nucleic acid sequence are present, the present method can be applied with modifications as follows: the signal detected at the relatively low detection temperature and the signal detected at the relatively median detection temperature are mathematically processed by using an initial reference value for a mixture of the first target nucleic acid sequence and the second target nucleic acid sequence to extract the signal for the third target nucleic acid sequence; wherein the initial reference value for a mixture of the first target nucleic acid sequence and the second target nucleic acid sequence is a value representing a relationship of change in signals provided by the first signal-generating means and the second signal-generating means at the relatively median detection temperature and the relatively low detection temperature.

Afterwards, the extracted signal for the second target nucleic acid sequence and the extracted signal for the third target nucleic acid sequence are each subjected to the step (c) of the method of the present invention, in order to identify whether each of the extracted signals satisfies an accuracy criterion.

As such, the signal extraction for three target nucleic acid sequences may be performed in a similar way to the signal extraction for two target nucleic acid sequences.

Therefore, it would be appreciated by one of skill in the art that the inventive method can be used to extract signals for three or more target nucleic acid sequences, with a slight modification thereof.

According to an embodiment, the incubation comprises a plurality of incubations and amended reference values for the incubations are individually determined.

The term used herein "a plurality of incubations" means incubations undertaken in different reaction vessels, tubes or wells. The advantages of the present invention become more highlighted for a plurality of incubations. Assumed that a plurality of incubations comprises certain combinations of "NG" target sequence and "CT" target sequence in unknown amounts, it would be general that the plurality of incubations is analyzed by using a single reference value for each target nucleic acid sequence. The present inventors have found that such utilization of a single reference value is likely to lead to erroneous detection results. According to an embodiment, an initial reference value for "NG" target sequence or an initial reference value for "CT" target sequence are applied to all of the incubations and then individually determined amended reference values are applied to the individual incubations if needed.

II. Storage Medium, Computer Program and Device for Signal Extraction

Since the storage medium, the device and the computer program of the prevent invention described hereinbelow are intended to perform the present methods in a computer, the common descriptions between them are omitted in order to avoid undue redundancy leading to the complexity of this specification.

In another aspect of this invention, there is provided a computer readable storage medium containing instructions to configure a processor to perform a method for extracting a signal for a target nucleic acid sequence from signals for two target nucleic acid sequences comprising a first target nucleic acid sequence and a second target nucleic acid sequence in a sample, the method comprising:

(a) receiving signal values from a signal-generating process with the sample at a relatively high detection temperature and a relatively low detection temperature; wherein the first target nucleic acid sequence in the sample is detected by a first signal-generating means and the second target nucleic acid sequence in the sample is detected by a second signal-generating means; wherein the detection is performed at one or more cycles of the signal-generating process to obtain a signal value at each of the one or more cycles; wherein signals to be generated by the two signal-generating means are not differentiated by a single type of detector;

(b) processing the signal values obtained in the step (a) by using a second initial reference value to extract the signal for the first target nucleic acid sequence or processing the signal values obtained in the step (a) by using a first initial reference value to extract the signal for the second target nucleic acid sequence; wherein the first initial reference value is a value representing a relationship of change in signals provided by the first signal-generating means at the relatively high detection temperature and the relatively low detection temperature, and the second initial reference value is a value representing a relationship of change in signals provided by the second signal-generating means at the relatively high detection temperature and the relatively low detection temperature; wherein the first initial reference value is predetermined from a control reaction using the first target nucleic acid sequence and the first signal-generating means and the second initial reference value is predetermined from a control reaction using the second target nucleic acid sequence and the second signal-generating means; and (c) identifying whether the extracted signal satisfies an accuracy criterion; when the extracted signal does not satisfy the accuracy criterion, the step (b) is repeated using an amended reference value instead of the initial reference value to re-extract the signal for the first target nucleic acid sequence or the second target nucleic acid sequence; wherein the amended reference value is determined such that the re-extracted signal satisfies the accuracy criterion.

According to an embodiment, the first initial reference value (or the second initial reference value) and its amended reference value are stored in the computer readable storage medium. According to an embodiment, the computer readable storage medium contains instructions to input the first initial reference value (or the second initial reference value) and its amended reference value in performing the method. According to an embodiment, the computer readable storage medium further contains instructions to configure a processor to perform a method for obtaining the first initial reference value (or the second initial reference value) and its amended reference value.

In still another aspect of this invention, there is provided a computer program to be stored on a computer readable storage medium to configure a processor to perform a method for extracting a signal for a target nucleic acid sequence from signals for two target nucleic acid sequences comprising a first target nucleic acid sequence and a second target nucleic acid sequence in a sample, the method comprising:

(a) receiving signal values from a signal-generating process with the sample at a relatively high detection temperature and a relatively low detection temperature; wherein the first target nucleic acid sequence in the sample is detected by a first signal-generating means and the second target nucleic acid sequence in the sample is detected by a second signal-generating means; wherein the detection is performed at one or more cycles of the signal-generating process to obtain a signal value at each of the one or more cycles; wherein signals to be generated by the two signal-generating means are not differentiated by a single type of detector;

(b) processing the signal values obtained in the step (a) by using a second initial reference value to extract the signal for the first target nucleic acid sequence or processing the signal values obtained in the step (a) by using a first initial reference value to extract the signal for the second target nucleic acid sequence; wherein the first initial reference value is a value representing a relationship of change in signals provided by the first signal-generating means at the relatively high detection temperature and the relatively low detection temperature, and the second initial reference value is a value representing a relationship of change in signals provided by the second signal-generating means at the relatively high detection temperature and the relatively low detection temperature; wherein the first initial reference value is predetermined from a control reaction using the first target nucleic acid sequence and the first signal-generating means and the second initial reference value is predetermined from a control reaction using the second target nucleic acid sequence and the second signal-generating means; and (c) identifying whether the extracted signal satisfies an accuracy criterion; when the extracted signal does not satisfy the accuracy criterion, the step (b) is repeated using an amended reference value instead of the initial reference value to re-extract the signal for the first target nucleic acid sequence or the second target nucleic acid sequence; wherein the amended reference value is determined such that the re-extracted signal satisfies the accuracy criterion.

According to an embodiment of the present invention, the computer program contains the first initial reference value (or the second initial reference value). According to an embodiment of the present invention, the computer program contains instructions to input the first initial reference value (or the second initial reference value) and its amended reference value in performing the method. According to an embodiment of the present invention, the computer program further contains instructions to configure a processor to perform a method for obtaining the first initial reference value (or the second initial reference value) and its amended reference value.

The program instructions are operative, when performed by the processor, to cause the processor to perform the present method described above. The program instructions for performing the present method may comprise an instruction to receive signal values from the signal-generating process with the sample at the relatively high detection temperature and the relatively low detection temperature; an instruction to process the signal values received for extracting a signal; and an instruction to identify whether the extracted signal satisfies an accuracy criterion. According to an embodiment, the program instructions for performing the present method may further comprise an instruction to obtain the first initial reference value (or the second initial reference value) and its amended reference value.

The present method described above is implemented in a processor, such as a processor in a stand-alone computer, a network attached computer or a data acquisition device such as a real-time PCR machine.

The types of the computer readable storage medium include various storage medium such as CD-R, CD-ROM, DVD, flash memory, floppy disk, hard drive, portable HDD, USB, magnetic tape, MINIDISC, nonvolatile memory card, EEPROM, optical disk, optical storage medium, RAM, ROM, system memory and web server.

The signal values from the signal-generating process may be received through several mechanisms. For example, the signal values may be acquired by a processor resident in a PCR data acquiring device. The signal values may be provided to the processor in real time as the signal values are being collected, or it may be stored in a memory unit or buffer and provided to the processor after the experiment has been completed. Similarly, the signal values may be provided to a separate system such as a desktop computer system via a network connection (e.g., LAN, VPN, intranet and Internet) or direct connection (e.g., USB or other direct wired or wireless connection) to the acquiring device, or provided on a portable medium such as a CD, DVD, floppy disk, portable HDD or the like to a stand-alone computer system. Similarly, the data set may be provided to a server system via a network connection (e.g., LAN, VPN, intranet, Internet and wireless communication network) to a client such as a notebook or a desktop computer system.

After the signal values have been received or acquired, the processing of the signal values undertakes to extract the signal for the first target nucleic acid sequence by the second initial reference value or to extract the signal for the second target nucleic acid sequence by the first initial reference value. The processor identifies whether the extracted signal satisfies the accuracy criterion. When the extracted signal does not satisfy the accuracy criterion, the step (b) is repeated using the amended reference value instead of the initial reference value.

The instructions to configure the processor to perform the present invention may be included in a logic system. The instructions may be downloaded and stored in a memory module (e.g., hard drive or other memory such as a local or attached RAM or ROM), although the instructions can be provided on any software storage medium such as a portable HDD, USB, floppy disk, CD and DVD. A computer code for implementing the present invention may be implemented in a variety of coding languages such as C, C++, Java, Visual Basic, VBScript, JavaScript, Perl and XML. In addition, a variety of languages and protocols may be used in external and internal storage and transmission of data and commands according to the present invention.

In a further aspect of this invention, there is provided a device for extracting a signal for a target nucleic acid sequence from signals for two target nucleic acid sequences comprising a first target nucleic acid sequence and a second target nucleic acid sequence in a sample, comprising (a) a computer processor and (b) the computer readable storage medium described above coupled to the computer processor.

According to an embodiment, the device further comprises a reaction vessel to accommodate the sample and signal-generating means, a temperature controlling means to control temperatures of the reaction vessel and/or a detector to detect signals at cycles.

According to an embodiment, the computer processor permits not only to receive a signal value at one or more cycles of the signal-generating process but also to process the signal values obtained for signal extraction by reference values and identify whether the extracted signal satisfies a predetermined accuracy criterion. The processor may be prepared in such a manner that a single processor can do several performances. Alternatively, the processor unit may be prepared in such a manner that several processors do the several performances, respectively.

According to an embodiment, the processor may be embodied by installing software into conventional devices for detection of target nucleic acid sequences (e.g. real-time PCR device).

For example, the present device may be embodied into a real-time PCR system. The system comprises a real-time PCR device for performing a real-time PCR amplification, and a computer system as a logic system connected to the real-time PCR device via a cable for extracting signal and displaying the correction resultants. The computer system may display the extraction resultants in various forms such as graphs, tables and words according to demands of users. The computer system may comprise instructions contained in a computer readable storage medium for performing the present method. The real-time PCR device and the computer system may be integrated into a system.

The signal values may be received with amplification curves in various fashions. For example, the signal values may be received and collected by a processor in a data collector of the real-time PCR device. Upon collecting the signal values, they may be provided to a processor in a real-time manner, or stored in a memory unit or buffer and then provided to a processor after experiments.

Likely, the signal values may be provided from the real-time PCR device to the computer system such as a desktop computer system via network connection (e.g., LAN, VPN, intranet and internet) or direct connection (e.g., USB and wired or wireless direct connections), or via portable media such as CD, DVD, floppy disk and portable HDD. Alternatively, the signal values may be provided to a server system via network connections (e.g., LAN, VPN, intranet, internet and wireless communication network) connected to a client such as notebook and desktop computer systems.

After the signal values are received or obtained, a signal-value processor proceeds to extract the signal by reference values. The signal extraction of the present invention may be undertaken by an application (i.e., program) installed into the computer system. Alternatively, it may be made by an application directly installed into the computer system through application store server or application provider servers in which the application is operable in an operating system of the computer system. The operating system includes Window, Macintosh and mobile operating systems such as iOS and Android that are installed into mobile terminals such as Smartphones and Tablet PC.

As described above, the present method for signal extraction may be embodied by an application (i.e., program) supplier-installed or user-direct installed into the computer system, and recorded in a computer readable storage medium.

A computer program embodying the present method may implement all functions for signal extraction. The computer program may a program comprising program instructions stored on a computer readable storage medium to configure a processor to perform the present method:

The computer program may be coded by using suitable computer languages such as C, C++, JAVA, Visual basic, VBScript, JavaScript, Perl, XML and machine languages. The program codes may include function codes for mathematical functions described above and control codes for implementing process in order by a processor of the computer system.

The codes may further comprise memory reference codes by which additional information or media required in implementing the above-described functions by the processor is referred at location (address) of internal or external memory of the computer system.

When the computer system requires communication with another computer or server in remote for implementing functions of the processor, the codes may further comprise communication-relating codes encoding how the processor is communicated with another computer or server in remote by using communication module (e.g., wired and/or wireless communication module) or what information or media is transmitted.

Functional programs and codes (code segments) for embodying the present invention may be easily inferred or modified by programmers in the art in considering system environments of computers reading storage media and executing programs.

The storage medium network-connected to the computer system may be distributed and computer-readable codes may be stored and executed in a distribution manner. In such case, at least one computer among a plurality of distributed computers may implement a portion of the functions and transmit results of the implementation to at least one computer that may also implement a portion of the functions and transmit results of the implementation to at least one computer.

The storage medium in which application (i.e., program) is recorded for executing the present invention includes a storage medium (e.g., hard disk) contained in application store servers or application provider servers, application provider servers per se, another computer having the program and its storage medium.

The computer system capable of reading the storage medium may include general PC such as desktop or notebook computers, mobile terminals such as Smartphone, Tablet PC, PDA (Personal Digital Assistants) and mobile communication terminals as well as all computing-executable devices.

III. Detection of Target Nucleic Acid

The extracted signal for the target nucleic acid sequence may be employed in the detection thereof. The detection of the target nucleic acid sequence comprises the determination of the presence of the target nucleic acid sequence in a sample. The target detection may be accomplished by various methods known in the art. For example, the target detection may be accomplished by applying a threshold to the plot of the extracted signal, and identifying whether there is a crossing point between the plot and the threshold. If there is a crossing point, the presence of the target nucleic acid sequence is determined; and if there is no crossing point, the absence of the target nucleic acid sequence is determined.

The features and advantages of this invention will be summarized as follows:

(a) The present invention using an amended reference value as well as an initial reference value enables to extract a signal for a target nucleic acid sequence in a more accurate, effective and reproducible manner, thereby overcoming shortcomings associated with method using a single reference value.

(b) The present invention can contribute to dramatic improvement in methods for detecting target nucleic acid sequences using different detection temperatures and reference values.

(c) The present invention using an amended reference value as well as an initial reference value can lead to increasing the detection accuracy in methods for detecting target nucleic acid sequences using different detection temperatures and reference values.

(d) In particular, in the case of RNA target detection using a degenerate primer set or lower concentration of a target nucleic acid sequence having a relatively low detection temperature, the usefulness of the present invention becomes more prominent.

(e) According to the present invention, more accurate signal extraction for detecting a target nucleic acid sequence is practical by developing a computer program for performing the present method for signal extraction.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1: Signal Detection and Extraction Based on MuDT1 Technology

According to an embodiment of MuDT1 technology, the first signal-generating means generates signals at the relatively high detection temperature and the relatively low detection temperature and the second signal-generating means generates a signal at the relatively low detection temperature, and the processing of the signal values is performed using the first initial reference value to extract the signal for the second target nucleic acid sequence from the signal at the relatively low detection temperature.

<1-1> Preparation of Templates and Oligonucleotides

The PTOCE method (WO 2012/096523) was used as a real-time PCR approach for detecting signals in a real-time manner at different detection temperatures.

Taq DNA polymerase having a 5' nuclease activity was used for the extension of upstream primers and downstream primers, the cleavage of PTO (Probing and Tagging Oligonucleotide), and the extension of PTO fragment. Genomic DNA of *Neisseria gonorrhoeae* (NG) and genomic DNA of *Chlamydia trachomatis* (CT) were used as target nucleic acid sequences.

The PTOs for detection of NG and CT by using the PTOCE method as signal-generating means comprise (i) a 5'-tagging portion comprising a nucleotide sequence non-complementary to the target nucleic acid sequence and (ii) a 3'-targeting portion comprising a hybridizing nucleotide sequence complementary to the target nucleic acid sequence. The CTOs (Capturing and Templating Oligonucleotides) comprise, in a 3' to 5' direction, (i) a capturing portion comprising a nucleotide sequence complementary to the 5'-tagging portion or a part of the 5'-tagging portion of the PTOs and (ii) a templating portion comprising a nucleotide sequence non-complementary to the 5'-tagging portion and the 3'-targeting portion of the PTOs. The CTOs were labeled with a quencher molecule (BHQ-2) at their 5'-ends and a fluorescent reporter molecule (CAL Fluor Red 610) in their templating portions. The PTOs and CTOs are blocked with a carbon spacer at their 3'-ends to prohibit their extension.

Because the PTOCE real-time method uses a single type of fluorescence label (CAL Fluor Red 610), signals for the target nucleic acid sequences cannot be differentiated from each other in a single reaction vessel by a single detector.

In the PTOCE real-time method, when a target sequence is present, the PTO hybridized with the target sequence is cleaved and a PTO fragment is produced. The PTO fragment is annealed to the capturing portion of the CTO, extended on the templating portion of the CTO and forms an extended duplex with the CTO (Duplexed CTO). The formation of the extended duplex provides a signal and an amplification curve can be obtained by measuring the signal at the extended duplex-forming temperature.

In this Example, the sequence and length of each extended duplex was designed such that the extended duplex for CT can be formed at 72° C. and the extended duplex for NG can be formed at 60° C. not at 72° C.

Accordingly, at the detection temperature of 72° C., only the signal for CT is detected, whereas at the detection temperature of 60° C., the signal for NG as well as the signal for CT is detected.

The sequences of upstream primers, downstream primers, PTOs, and CTOs used in this Example are described in Table 1.

TABLE 1

| Name | Type | Sequence (5' → 3') | SEQ ID |
|------|------|--------------------|--------|
| NG_F | Primer | TACGCCTGCTACTTTCACGCTIIIII GTAATCAGATG | SEQ ID NO: 1 |

TABLE 1-continued

| Name | Type | Sequence (5' → 3') | SEQ ID |
|------|------|---------------------|--------|
| NG_R | Primer | CAATGGATCGGTATCACTCGCIIIII CGAGCAAGAAC | SEQ ID NO: 2 |
| NG_PTO | PTO | GTACGCGATACGGGCCCCTCATTGGC GTGTTTCG[C3 spacer] | SEQ ID NO: 3 |
| NG_CTO | CTO | [BHQ-2]TTTTTTTTTTTTTTTTTT G[T(Cal Fluor Red 610)]ACT GCCCGTATCGCGTAC[C3 spacer] | SEQ ID NO: 4 |
| CT_F | Primer | GAGTTTTAAAATGGGAAATTCTGGTI IIIITTTGTATAAC | SEQ ID NO: 5 |
| CT_R | Primer | CCAATTGTAATAGAAGCATTGGTTGI IIIITTATTGGAGA | SEQ ID NO: 6 |
| CT_PTO | PTO | GATTACGCGACCGCATCAGAAGCTGT CATTTTGGCTGCG[C3 spacer] | SEQ ID NO: 7 |
| CT_CTO | CTO | [BHQ-2]GCGCTGGATACCCTGGACG A[T(Cal Fluor Red 610)]ATG TGCGGTCGCGTAATC[C3 spacer] | SEQ ID NO: 8 |

I: Deoxyinosine
PTO: Probing and Tagging Oligonucleotide
CTO: Capturing and Templating Oligonucleotide
BHQ: Quencher (Black Hole Quencher)
Underlined letter: 5'-tagging portion of PTO <1-2> Real-Time PCR and Signal Detection at Different Temperatures The real-time PCR in accordance with the PTOCE method was conducted in the final volume of 20 μl containing a target nucleic acid (10 pg or 100 fg of NG or CT genomic DNA, a mixture of 10 pg of NG genomic DNA and 100 fg of CT genomic DNA, a mixture of 100 fg of NG genomic DNA and 100 fg of CT genomic DNA, or a mixture of 100 fg of NG genomic DNA and 10 pg of CT genomic DNA), 5 pmole of upstream primer (SEQ ID NO:1), 5 pmole of downstream primer (SEQ ID NO:2), 3 pmole of PTO (SEQ ID NO:3) and 1 pmole of CTO (SEQ ID NO:4) for NG target amplification, 5 pmole of upstream primer (SEQ ID NO:5), 5 pmole of downstream primer (SEQ ID NO:6), 3 pmole of PTO (SEQ ID NO:7) and 1 pmole of CTO (SEQ ID NO:8) for CT target amplification, and 5 μl of 4× Master Mix (final conc., 200 μM dNTPs, 2 mM $MgCl_2$, 2 U of Taq DNA polymerase) (Enzynomics, Korea). The tubes containing the reaction mixture were placed on the real-time thermocycler (CFX96 Real-time Cycler, Bio-Rad) for 5 min at 50° C., denatured for 15 min at 95° C. and subjected to 50 cycles of 30 sec at 95° C., 60 sec at 60° C., 30 sec at 72° C. Detection of signals was performed at 60° C. and 72° C. at each cycle. The results are represented by FIGS. 2A and 2B.

As shown in FIG. 2A, for the sample containing only NG target (10 pg or 100 fg), signals were detected at 60° C. but not at 72° C.; for the sample containing only CT target (10 pg or 100 fg), signals were detected both at 60° C. and at 72° C.

As shown in FIG. 2B, for the sample containing both NG and CT targets (10 pg NG+100 fg CT; 100 fg NG+100 fg CT; and 100 fg NG+10 pg CT), signals were detected both at 60° C. and at 72° C.; for the sample containing no target (NTC), signals were not detected at 60° C. and at 72° C.

<1-3> Extraction of Signal for a Target Nucleic Acid Sequence

As represented in FIGS. 2A and 2B, signals for CT target can be directly taken from signals detected at 72° C., since these are detected only at 72° C. In contrast, signals for NG target are not detected at 72° C. but at 60° C. together with signals for CT target, and signals for CT target has to be therefore removed from signals at 60° C. for extraction of signals for NG target. It is noted that the signal intensities for target nucleic acid, particularly CT, vary depending upon the temperatures for detection, i.e., the intensity of signals at 60° C. may be higher than that at 72° C. Accordingly, signals for CT target detected at 72° C. should be appropriately transformed into signals to be expected at 60° C. For this purpose, a reference value was used in this method.

Specifically, signals for NG target can be extracted by using a reference value representing a relationship of change in signals at 72° C. and 60° C. for CT target in accordance with the Equation I-1:

$$\text{Extracted signal for the second target nucleic acid sequence} = [\text{signal at the relatively low detection temperature}] - [(\text{signal at the relatively high detection temperature}) \times (\text{the first initial reference value})]; \quad \text{<Equation I-1>}$$

wherein, the second target nucleic acid sequence is NG target, the relatively low detection temperature is 60° C. and the relatively high detection temperature is 72° C. and the first initial reference value is a reference value for CT target.

The extracted signal for NG target can be plotted.

An initial reference value for CT target may be calculated in accordance with the Equation III-1:

$$\text{Initial reference value for CT target} = [\text{signal at 60° C. for a control sample containing only CT target}] \div [\text{signal at 72° C. for a control sample containing only CT target}] \quad \text{<Equation III-1>}$$

The reference value for CT target may vary depending upon the condition of the reaction. Accordingly, some different reference values for CT may be obtained from iterative experiments. That is, the reference value for CT may be obtained in a certain range of values from a control sample containing only CT target.

It would be general to one of skill in the art that reference values for CT target are obtained in a certain range from a control sample containing only CT target and a single suitable reference value among the reference values is suitably selected to remove signals for CT target from signals at 60° C. The present inventors have found that the application of the single reference value for CT target to all reactions may cause erroneous signals when the single reference value is unsuitable to an individual reaction.

Figure 3:
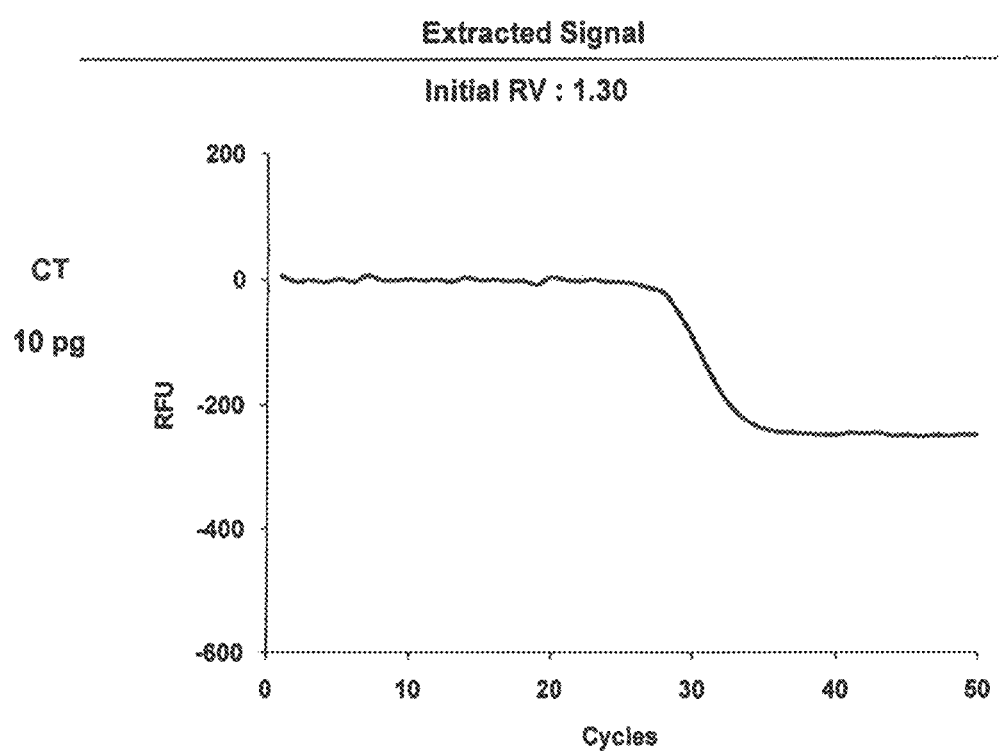
FIG. 3 represents an embodiment of a signal extraction for the sample containing 10 pg of CT target. A signal for the second target nucleic acid sequence (NG) was extracted by using (i) an initial reference value for the first target nucleic acid sequence (CT) of 1.30 and (ii) signals detected at the relatively low detection temperature (60° C.) and the relatively high detection temperature (72° C.), in accordance with the mathematical equation I-1.

For example, a pattern of signal for NG target, which was extracted from signal at 60° C. for a sample containing 10 pg of CT target by using a single reference value of 1.30, is shown in FIG. 3. As the sample contains only CT target, the signal for NG target extracted by removal of CT target signal should be theoretically around RFU 0 at all cycles when a suitable single reference value for CT target is applied. Unlike such expectation, the application of the single reference value for CT target (1.30) generated erroneous signals below the threshold due to removal of signals larger than signals originated from CT target. The erroneous signal addresses that the single reference value is not suitable to the sample and a new reference value smaller than the single reference value is required.

These results demonstrate that when a single reference value is applied to all reactions for signal extraction for a target nucleic acid sequence, erroneous signals may be generated due to unsuitability of the reference value to certain samples.

Example 2: Signal Re-Extraction by Using an Amended Reference Value Based on MuDT1 Technology The present inventors adopted an amended reference value to replace the unsuitable reference value as Example 1. The extraction of a signal for a target nucleic acid sequence was executed by using an initial reference value. When the extracted signal did not satisfy a predetermined accuracy criterion, the initial reference value was considered to be unsuitable to analysis of the sample and then the signal re-extraction was performed by using an amended reference value. The accuracy criterion was used to evaluate whether extracted signals exhibited theoretically predictable signal pattern or not (i.e., non-erroneous signals or not). In particular, the accuracy criterion was that the extracted signal had no signal value crossing a predetermined threshold. Therefore, when the extracted signal had a signal value crossing the predetermined threshold, the amended reference value was determined and applied.

The determination and application of the amended reference value may be performed in two alternative fashions: (i) Fixed amended-reference value approach; and (ii) Variable amended-reference value approach. In the fixed amended-reference value approach, the amended reference value determined based on signal at a certain cycle is applied to all cycles. In the variable amended-reference value approach, each additional amended reference value determined based on signal of each cycle before a certain cycle and the amended reference value determined based on a signal at the certain cycle are distinctly applied to cycles before the certain cycle and to cycles after the certain cycle, respectively. The details of the two approaches are as follows:

<2-1> Fixed Amended-Reference Value Approach

The fixed amended-reference value approach is schematically represented by FIG. 4A.

The experimental results in Example 1 (FIGS. 2A and 2B) were subjected to mathematical processing by using the initial reference value of 1.30 for signal extraction of NG target. The accuracy criterion that the extracted signal does not cross a predetermined threshold RFU −100 was used as the predetermined threshold. Where the extracted signal had a signal value crossing the threshold, the initial reference value was considered to be unsuitable and required for amendment. Where the extracted signal had no signal value crossing the threshold, the initial reference value was considered to be suitable and the amended reference value was no longer required. Where the amendment of the initial reference value was required, a cycle having the lowest RFU was selected as a cycle for calculation of the amended reference value, named as PARV (point for setting an amended reference value) (see FIG. 4A, the upper part). Afterwards, the amended reference value at PARV was calculated based on signals of the samples at 60° C. and 72° C., named as amended RV (reference value) at PARV in accordance with Equation IV-1 (see FIG. 4A, the middle part).

Amended Reference value for CT target=[signal at 60° C. for a sample being analyzed]÷[signal at 72° C. for a sample being analyzed]  <Equation IV-1>

The amended RV at PARV was applied to all cycles of signals of the sample at 72° C. for the signal re-extraction of NG target in accordance with mathematical equation I-1, followed by signal re-extraction (see FIG. 4A, the lower part). By the signal re-extraction, erroneous signal pattern generated by the signal extraction was corrected.

Furthermore, we evaluated whether the fixed amended-reference value approach could be successfully applied to other samples. The samples containing various concentrations of NG, CT or a mixture of NG and CT underwent signal re-extraction of NG target by the fixed amended-reference value approach (see FIGS. 4B and 4C).

Figure 4B:
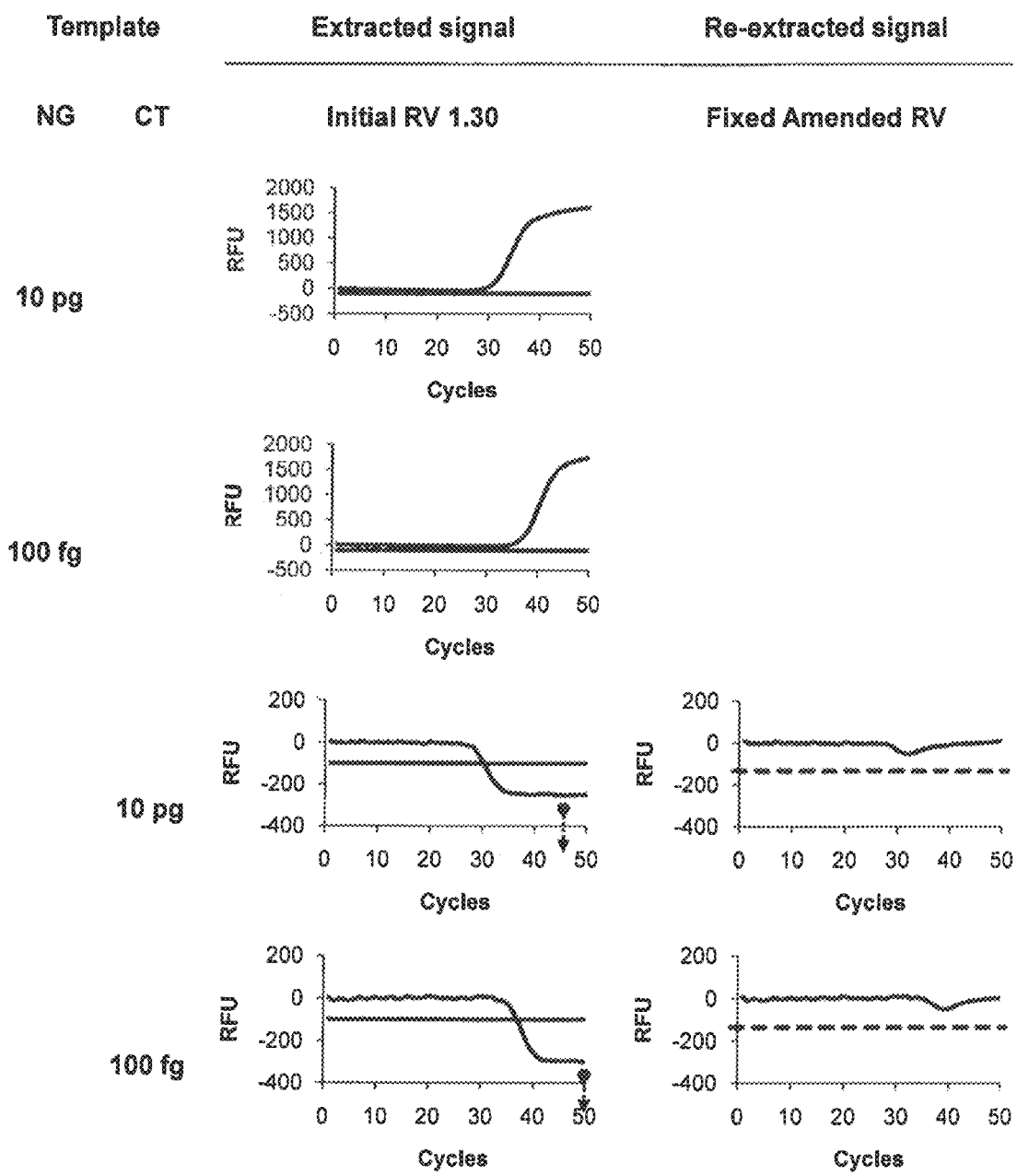

As shown in FIGS. 4B and 4C, the extracted signal for the sample containing only NG target had no a signal value crossing the threshold and therefore did not require an amended reference value. The extracted signals for the samples containing only CT target or a mixture of 100 fg of NG and 10 pg of CT had a signal value crossing the threshold and therefore an amended reference value was determined and applied. Following the application of the amended reference value, the re-extracted signals for the sample containing only CT target were rendered to have signal values around RFU 0 and the re-extracted signals for the sample containing a mixture of NG and CT targets to have positive signal values, which addresses that the signals for NG target were correctly re-extracted in all the samples. FIG. 4D represents the initial reference values, PARV and the fixed amended-reference values at PARV applied to each reaction.

These results urge us to reason that the fixed amended-reference value approach in detection of multiple target nucleic acid sequences at different detection temperatures using a single detection channel permits to amend erroneous signals due to unsuitable reference values, thereby enabling to detect target nucleic acid sequences in more accurate manner.

<2-2> Variable Amended-Reference Value Approach

The variable amended-reference value approach is schematically represented by FIG. 5A.

The experimental results in Example 1 (see FIGS. 2A and 2B) were subjected to mathematical processing by using the initial reference value of 1.30 for signal extraction of NG target. The accuracy criterion that the extracted signal does not cross a predetermined threshold RFU −100 was used as the predetermined threshold. Where the extracted signal had a signal value crossing the threshold, the initial reference value was considered to be unsuitable and required for amendment. Where the extracted signal had no signal value crossing the threshold, the initial reference value was considered to be suitable and the amended reference value was no longer required. Where the amendment of the initial reference value was required, a cycle having the lowest RFU was selected as a cycle for calculation of the amended reference value, PARV (see FIG. 5A, the upper part). Afterwards, the amended reference values at PARV and each of cycles before PARV were calculated based on signals of the samples at 60° C. and 72° C. in accordance with mathematical equation IV-1 (see FIG. 5A, the middle part). The amended reference value at each of cycles before PARV was applied to each cycle before PARV and the amended reference value at PARV was applied to all cycles after PARV, followed by signal re-extraction (see FIG. 5A, the lower part). By the signal re-extraction, erroneous signal pattern was corrected.

Furthermore, we evaluated whether the variable amended-reference value approach could be successfully applied to other samples. The samples containing various concentrations of NG, CT or a mixture of NG and CT underwent signal re-extraction of NG target by the variable amended-reference value approach (see FIGS. 5B and 5C).

Figure 5B:
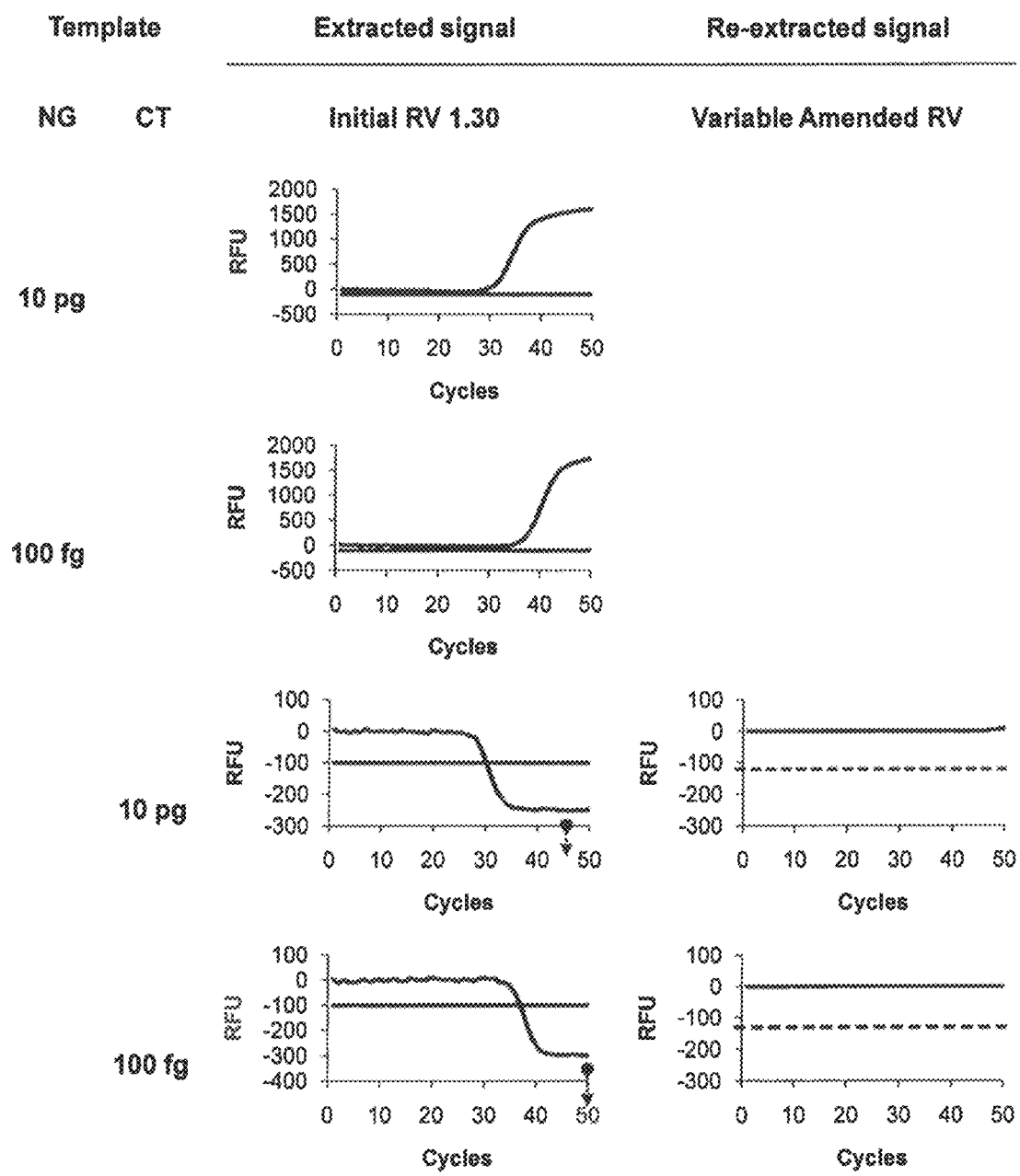
FIGS. 5B and 5C represent results of signal extraction and re-extraction according to the variable amended-reference value approach, for samples containing various concentrations of NG, CT or a mixture of NG and CT. A signal extraction was performed by using an initial reference value of 1.30. Where the extracted signal did not satisfy the accuracy criterion, a signal re-extraction was performed in accordance with the variable amended-reference value approach. In the figure, 'Initial RV' represents the initial reference value for CT; 'Variable Amended RV' represents the amended reference value for CT calculated by the signals at PARV and the signal at each cycle; and the dotted lines represent the threshold for determining the suitability of the RV from extracted signals
Figure 5C:
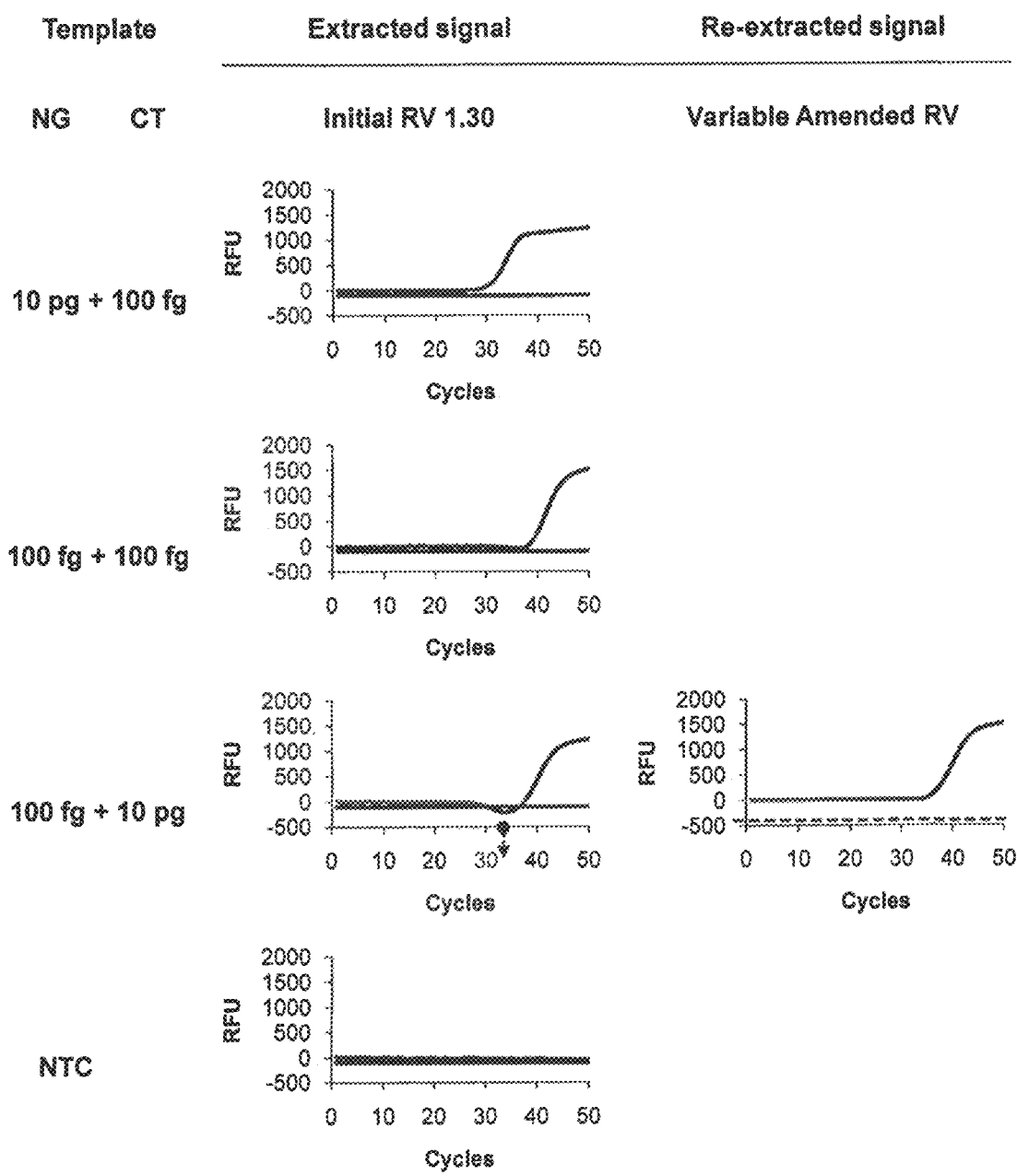

As shown in FIGS. 5B and 5C, the extracted signal for the sample containing only NG target had no a signal value crossing the threshold and therefore did not require an amended reference value. The extracted signals for the samples containing only CT target or a mixture of 100 fg of NG and 10 pg of CT had a signal value crossing the threshold and therefore amended reference values were determined and applied. Following the application of the amended reference values, the re-extracted signals for the sample containing only CT target were rendered to have signal values around RFU 0 and the re-extracted signals for the sample containing a mixture of NG and CT targets to have positive signal values, addressing that the signals for NG target were correctly re-extracted in all the samples. FIG. 5D represents the initial reference values, PARV and the variable amended-reference values at PARV applied to each reaction.

Alternatively, the accuracy criterion that the extracted signal has a signal value of more than a predetermined threshold may be used. When the extracted signal has a signal value of not more than a predetermined threshold, the initial reference value is considered to be unsuitable and required for amendment. Employment of the alternative criterion can provide similarly corrected results.

These results urge us to reason that the variable amended-reference value approach in detection of multiple target nucleic acid sequences at different detection temperatures using a single detection channel permits to amend erroneous signals due to unsuitable reference values, thereby enabling to detect target nucleic acid sequences in more accurate manner.

Example 3: Signal Detection and Extraction Based on MuDT2 Technology

According to an embodiment of MuDT2 technology, the two signal-generating means generate signals at the relatively high detection temperature and the relatively low detection temperature. The processing of the signal values is performed to extract the signal for the second target nucleic acid sequence by the first initial reference value from the signal at the relatively low detection temperature or the signal at the relatively high detection temperature. Likewise, the processing of the signal values is performed to extract the signal for the first target nucleic acid sequence by the second initial reference value from the signal at the relatively low detection temperature or the signal at the relatively high detection temperature.

<3-1> Preparation of Templates and Oligonucleotides

The TaqMan method was used as a real-time PCR approach for detecting signals in a real-time manner at different detection temperatures.

Taq DNA polymerase having a 5' nuclease activity was used for the extension of upstream primers and downstream primers and the cleavage of TaqMan probes. Genomic DNA of *Neisseria gonorrhoeae* (NG) and genomic DNA of *Chlamydia trachomatis* (CT) were used as target nucleic acid sequences.

Where a target nucleic acid is present in the TaqMan real-time PCR, a TaqMan probe is cleaved and a labeled fragment is released. The release of the labeled fragment provides a signal and an amplification curve can be obtained by measuring the signal from the labeled fragment.

A TaqMan probe for NG was labeled with a fluorescent reporter molecule (Quasar 670) at its 5'-end and a quencher molecule at its 3'-end (SEQ ID NO: 9) and a TaqMan probe for CT with a fluorescent reporter molecule (Quasar 670) at its 5'-end and a quencher molecule at its internal site (BHQ-2) (SEQ ID NO: 12).

In this Example, a signal for NG and a signal for CT are both detected at 60° C. and 72° C. The TaqMan probes used for the two targets provide different relationships in a signal change between the two detection temperatures (i.e., different reference values). In particular, the TaqMan probes were designed in this Example such that the difference in signals at 60° C. and 72° C. for CT was higher than that for NG.

The sequences of upstream primers, downstream primers, and TaqMan probes used in this Example are described in Table 2.

TABLE 2

| Name | Type | Sequence (5' → 3') | SEQ ID |
|---|---|---|---|
| NG_F | Primer | TACGCCTGCTACTTTCACGCTIIIII GTAATCAGATG | SEQ ID NO: 1 |
| NG_R | Primer | CAATGGATCGGTATCACTCGCIIIII CGAGCAAGAAC | SEQ ID NO: 2 |
| NG_P | TaqMan Probe | [Quasar 670]TGCCCCTCATTGGC GTGTTTCG[BHQ-2] | SEQ ID NO: 9 |
| CT2_F | Primer | TCCGAATGGATAAAGCGTGACIIIII ATGAACTCAC | SEQ ID NO: 10 |
| CT2_R | Primer | AACAATGAATCCTGAGCAAAGGIIII ICGTTAGAGTC | SEQ ID NO: 11 |
| CT2_P | TaqMan Probe | [Quasar 670]CATTGTAAAGA[T (BHQ-2)]ATGGTCTGCTTCGACCG [C3 spacer] | SEQ ID NO: 12 |

I: Deoxyinosine
BHQ: Quencher (Black Hole Quencher)

<3-2> Real-Time PCR and Signal Detection at Different Temperatures

The real-time PCR in accordance with the TaqMan method was conducted in the final volume of 20 µl containing a target nucleic acid (10 pg or 1 pg of NG or CT genomic DNA, a mixture of 10 pg of NG genomic DNA and 1 pg of CT genomic DNA, a mixture of 10 pg of NG genomic DNA and 10 pg of CT genomic DNA, or a mixture of 1 pg of NG genomic DNA and 10 pg of CT genomic DNA), 5 pmole of upstream primer (SEQ ID NO:1), 10 pmole of downstream primer (SEQ ID NO:2) and 1.5 pmole of TaqMan probe (SEQ ID NO:9) for NG target amplification, 5 pmole of upstream primer (SEQ ID NO:10), 10 pmole of downstream primer (SEQ ID NO:11) and 3 pmole of TaqMan probe (SEQ ID NO:12) for CT target amplification, and 5 µl of 4× Master Mix (final conc., 200 µM dNTPs, 2 mM MgCl$_2$, 2 U of Taq DNA polymerase) (Enzynomics, Korea). The tubes containing the reaction mixture were placed on the real-time thermocycler (CFX96 Real-time Cycler, Bio-Rad) for 5 min at 50° C., denatured for 15 min at 95° C. and subjected to 50 cycles of 30 sec at 95° C., 60 sec at 60° C., 30 sec at 72° C. Detection of signals was performed at 60° C. and 72° C. at each cycle. The results are represented in FIGS. 6A and 6B.

Figure 6A:
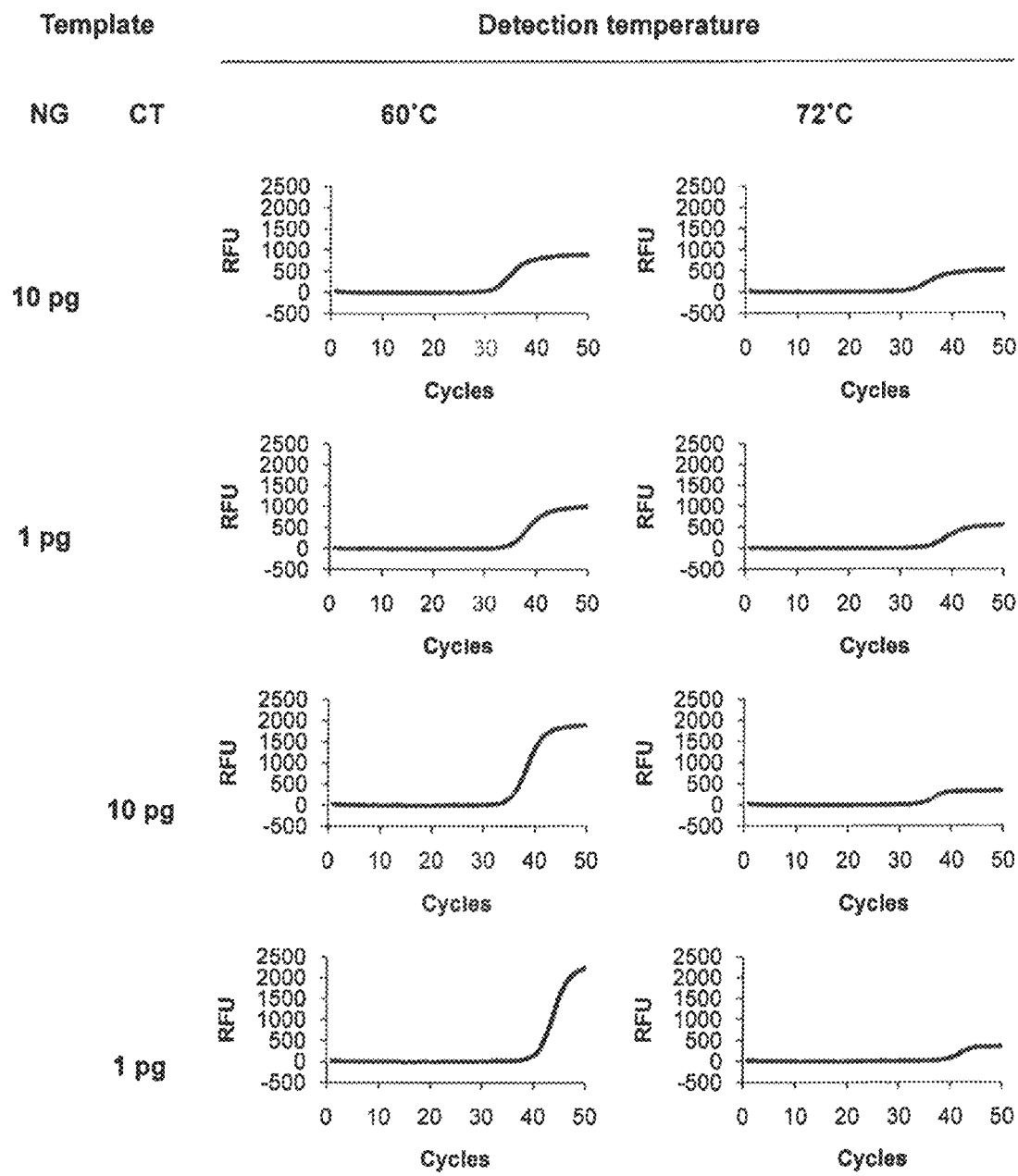
FIGS. 6A and 6B represent signals detected at different detection temperatures of 60° C. and 72° C. in accordance with a TaqMan real-time PCR method (MuDT2 Technology), for samples containing genomic DNA of *Neisseria gonorrhoeae* (NG), genomic DNA of *Chlamydia trachomatis* (CT) or mixture of NG and CT.

As shown in FIGS. 6A and 2B, signals were detected both at 60° C. and 72° C. in the presence of NG, CT, or NG+CT targets and not detected in the absence of targets (NTC).

<3-3> Extraction of Signal for a Target Nucleic Acid Sequence

Figure 6B:
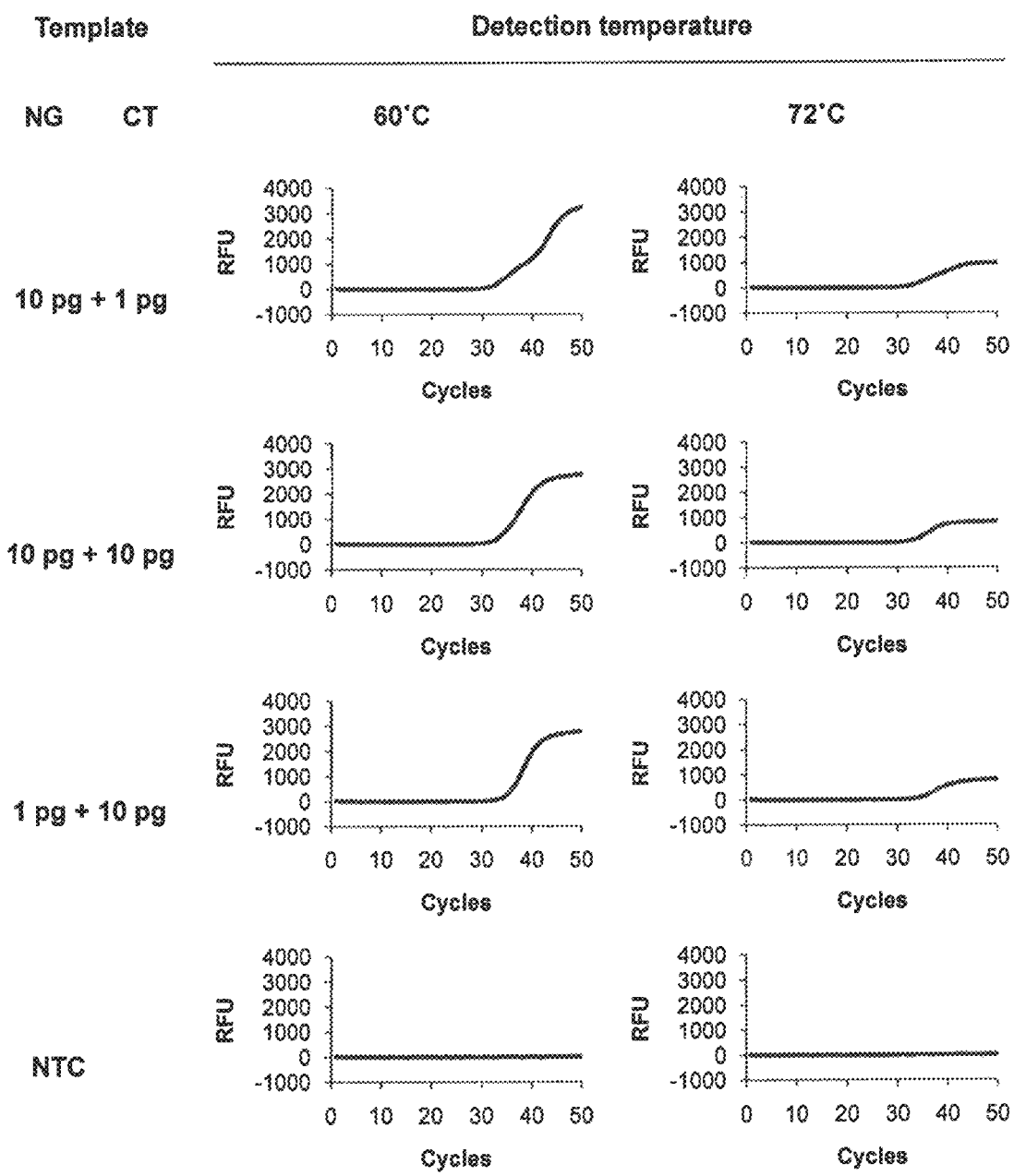

As represented in FIGS. 6A and 6B, signals for each target cannot be directly taken from signals detected at 60° C. or 72° C. Therefore, signals for the other target have to be removed from signals at each detection temperature for extraction of signals for each target.

Signals for each target can be extracted by using a reference value representing a relationship of change in signals at 72° C. and 60° C. for each target. In this Example, signals were extracted in accordance with the mathematical equation I-1 and mathematical equation I-4:

> Extracted signal for the second target nucleic acid sequence=[signal at the relatively low detection temperature]−[(signal at the relatively high detection temperature)×(the first initial reference value)];   <Equation I-1> wherein, the second target nucleic acid sequence is CT target; and the first initial reference value is a ratio of the signal provided by the first signal-generating means at the relatively low detection temperature to the signal provided by the first signal-generating means at the relatively high detection temperature.

> Extracted signal for the first target nucleic acid sequence=[signal at the relatively high detection temperature]−[(signal at the relatively low detection temperature)÷(the second initial reference value)];   <Equation I-4> wherein, the first target nucleic acid sequence is NG target; and the second initial reference value is a ratio of the signal provided by the second signal-generating means at the relatively low detection temperature to the signal provided by the second signal-generating means at the relatively high detection temperature.

The extracted signal for each target can be plotted.

The reference value for each target may be calculated in accordance with the mathematical equations III-1 and III-2:

> Initial reference value for CT target=[signal at 60° C. for a control sample containing only CT target]÷[signal at 72° C. for a control sample containing only CT target]   <Equation III-1>

> Initial reference value for NG target=[signal at 60° C. for a control sample containing only NG target]÷[signal at 72° C. for a control sample containing only NG target]   <Equation III-2>

Figure 7A:
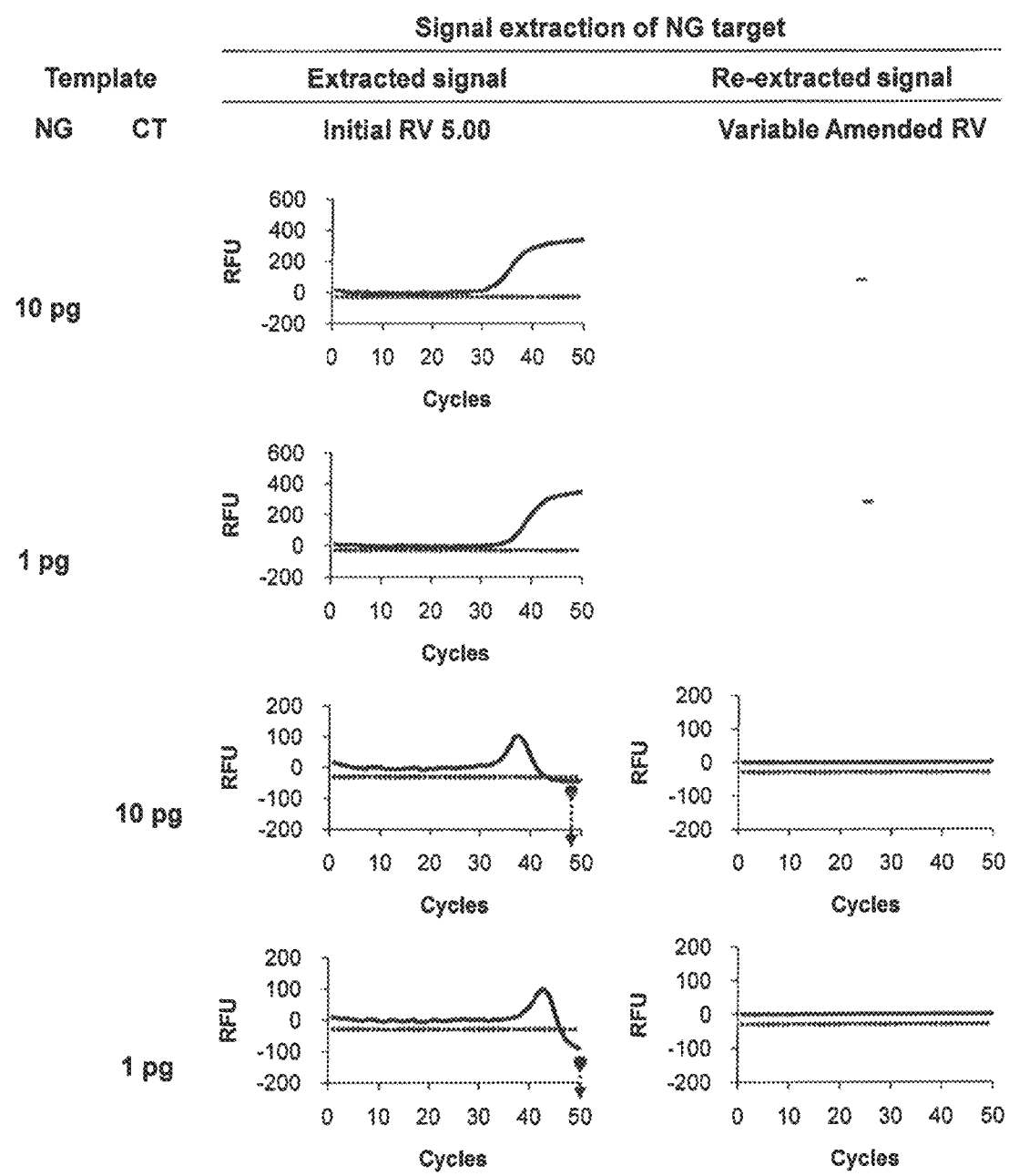
FIGS. 7A and 7B represent results of signal extraction and re-extraction of NG target according to the variable amended-reference value approach, for samples containing various concentrations of NG, CT or a mixture of NG and CT. A signal extraction was performed by using an initial reference value of 5.00. Where the extracted signal did not satisfy the accuracy criterion, a signal re-extraction was performed in accordance with the variable amended-reference value approach. In the figure, 'Initial RV' represents the initial reference value for CT; 'Variable Amended RV' represents the amended reference value for CT calculated by the signals at PARV and the signal at each cycle; and the dotted lines represent the threshold for determining the suitability of the RV from extracted signals.
Figure 7B:
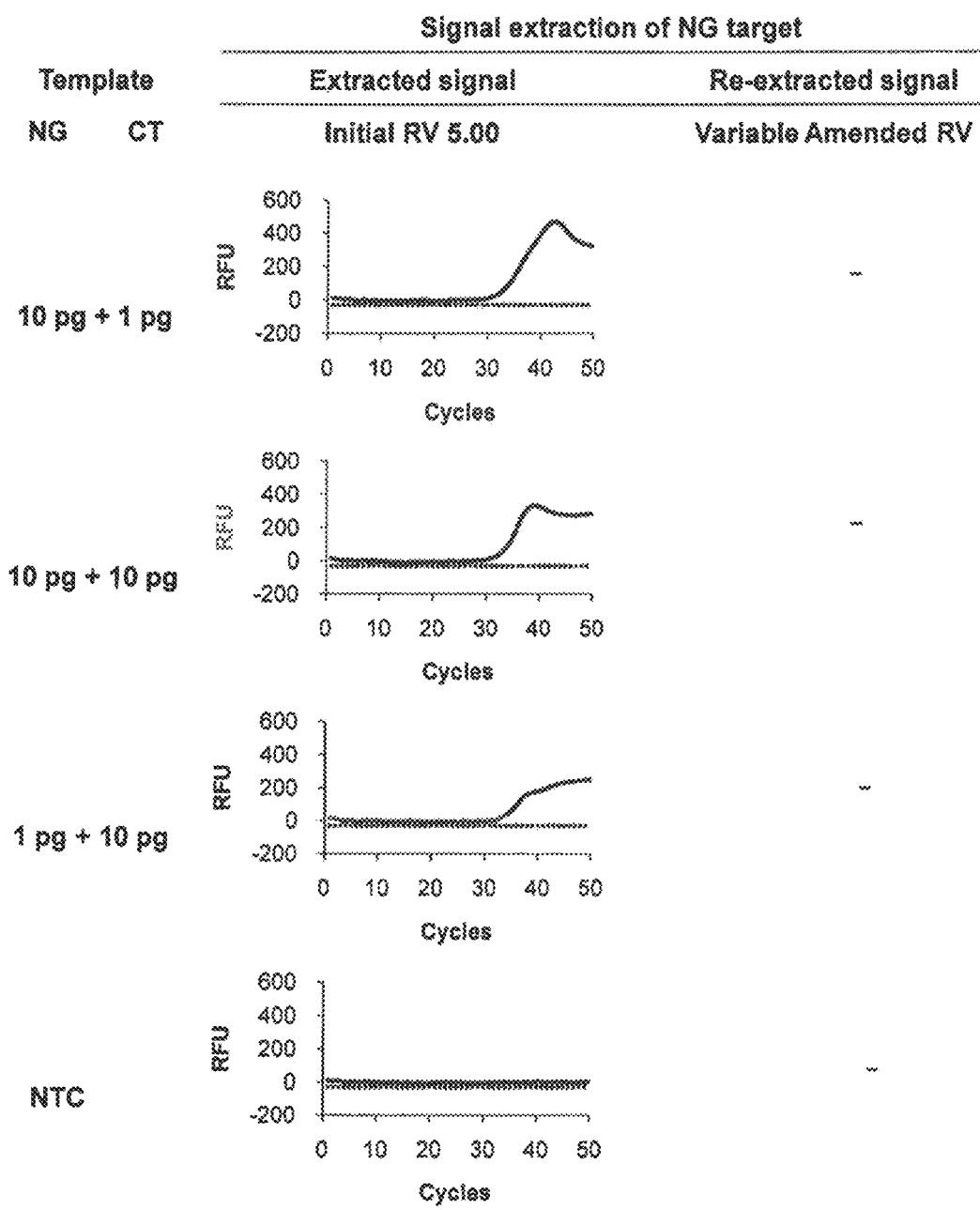

As shown in FIGS. 7A and 7B, the signal for NG target was extracted from signal at 72° C. by using an initial reference value for CT target. The initial reference value for CT was predetermined as "5.00". The application of the initial reference value for CT target (5.00) generated erroneous signals below the threshold due to removal of signals larger than signals originated from CT target in a sample containing 10 pg or 1 pg of CT target (see FIG. 7A). The erroneous signal addresses that the initial reference value is not suitable and a new reference value of greater than the initial reference value is required.

Figure 7D:
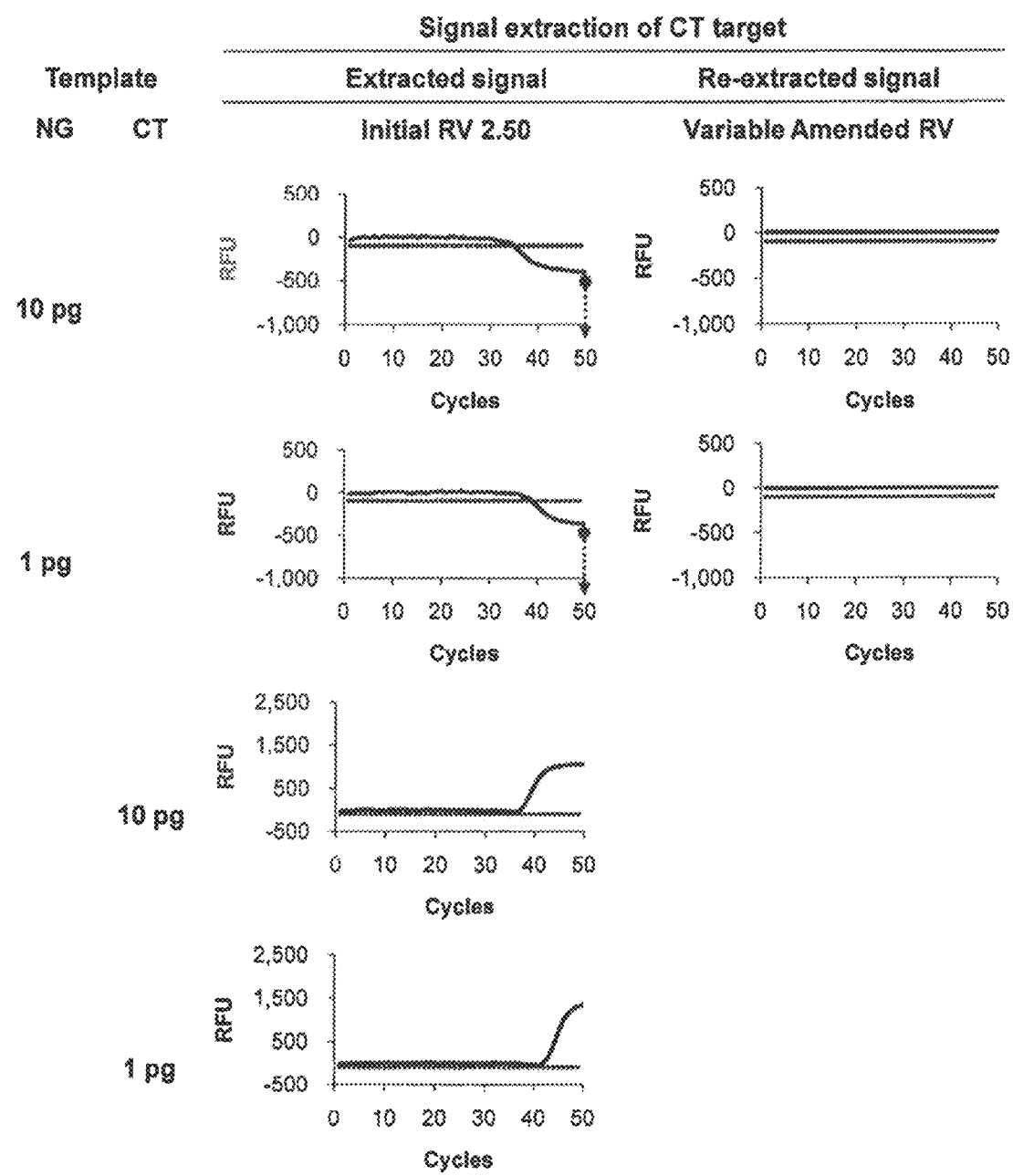
FIGS. 7D and 7E represent results of signal extraction and re-extraction of CT target according to the variable amended-reference value approach, for samples containing various concentrations of NG, CT or a mixture of NG and CT. A signal extraction was performed by using an initial reference value of 2.50. Where the extracted signal did not satisfy the accuracy criterion, a signal re-extraction was performed in accordance with the variable amended-reference value approach. In the figure, 'Initial RV' represents the initial reference value for NG; 'Variable Amended RV' represents the amended reference value for NG calculated by the signals at PARV and the signal at each cycle; and the dotted lines represent the threshold for determining the suitability of the RV from extracted signals.
Figure 7E:
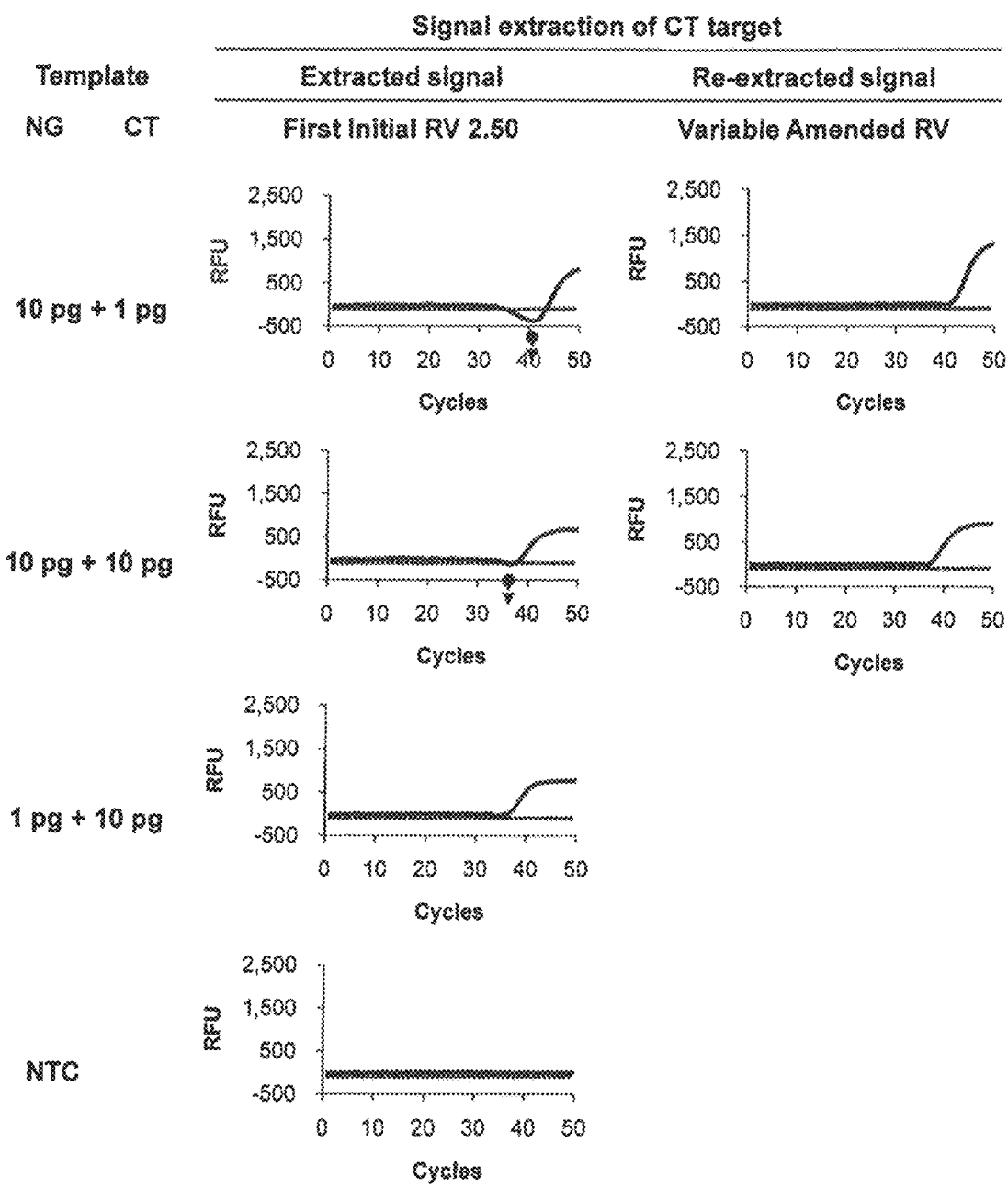

As shown in FIGS. 7D and 7E, the signal for CT target was extracted from signal at 60° C. by using an initial reference value for NG target. The application of the initial reference value for NG target (2.50) generated erroneous signals below the threshold due to removal of signals larger than signals originated from NG target (see FIGS. 7D and 7E). The erroneous signal addresses that the initial reference value is not suitable and a new reference value smaller than the initial reference value is required.

These results demonstrate that when a single reference value is applied to all reactions for signal extraction for a target nucleic acid sequence, erroneous signals are generated due to unsuitability of the reference value to certain samples.

Example 4: Signal Re-Extraction by Using an Amended Reference Value Based on MuDT2 Technology The accuracy criterion was used to evaluate whether extracted signals exhibited theoretically predictable signal pattern or not (i.e., non-erroneous signals or not). In particular, the accuracy criterion was that the extracted signal had no signal value crossing a predetermined threshold. Therefore, when the extracted signal had a signal value crossing the predetermined threshold, the amended reference value was determined and applied. The determination and application of the amended reference value were performed according to "Variable amended-reference value approach" described in the <Example 2>.

The experimental results in Example 3 (see FIGS. 6A and 6B) were subjected to mathematical processing by using the initial reference value of 5.00 for signal extraction of NG target. The accuracy criterion that the extracted signal does not cross a predetermined threshold RFU −30 was used as the predetermined threshold.

As shown in FIG. 7A, the extracted signals for the samples containing only CT target had a signal value crossing the predetermined threshold and therefore an amended reference value was applied. As a result, it was elucidated that the erroneous signal pattern generated by the signal extraction was corrected by the signal re-extraction. FIG. 7C represents the initial reference values, PARV and the variable amended-reference values at PARV applied to the reaction results.

The experimental results in Example 3 (FIGS. 6A and 6B) were subjected to mathematical processing by using the initial reference value of 2.50 for signal extraction of CT target. The accuracy criterion that the extracted signal does not cross a predetermined threshold RFU −100 was used as the predetermined threshold.

As shown in FIGS. 7D and 7E, the extracted signals for the samples containing only NG target, a mixture of 10 pg of NG and 1 pg of CT, or a mixture of 10 pg of NG and 10 pg of CT had a signal value crossing the threshold and therefore an amended reference value was determined and applied. As a result, it was verified that the erroneous signal pattern generated by the signal extraction was corrected by the signal re-extraction. FIG. 7F represents the initial reference values, PARV and the variable amended-reference values at PARV applied to the reaction results.

These results urge us to reason that the variable amended-reference value approach in detection of multiple target nucleic acid sequences at different detection temperatures using a single detection channel permits to amend erroneous signals due to unsuitable reference values, thereby enabling to detect target nucleic acid sequences in more accurate manner.

The present method utilizing an amended reference value can improve methods for detection of multiple target nucleic acid sequences at different detection temperatures using a single detection channel to amend erroneous signals due to unsuitable reference values. Consequently, the present invention enables to detect target nucleic acid sequences in more accurate manner.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for extracting a signal for a target nucleic acid sequence from signals for two target nucleic acid sequences in a sample, comprising:
   (a) incubating the sample with a first signal-generating means capable of generating a signal for a first target nucleic acid sequence and a second signal-generating means capable of generating a signal for a second target nucleic acid sequence in a single reaction vessel, and detecting signals at a relatively high detection temperature and a relatively low detection temperature by the single type of detector; wherein the incubation is performed by a signal-generating process; wherein the detection is performed at one or more cycles of the signal-generating process to obtain a signal value at each of the one or more cycles; and wherein the two signals to be generated by the two signal-generating means are not differentiated by a single type of detector;
   (b) processing the signal values obtained in the step (a) by:
      using a second initial reference value to extract the signal for the first target nucleic acid sequence; or
      using a first initial reference value to extract the signal for the second target nucleic acid sequence;
   wherein the first initial reference value is a value representing a relationship of change in signals provided by the first signal-generating means at the relatively high detection temperature and the relatively low detection temperature, and the second initial reference value is a value representing a relationship of change in signals provided by the second signal-generating means at the relatively high detection temperature and the relatively low detection temperature; and wherein the first initial reference value is predetermined from a control reaction using the first target nucleic acid sequence and the first signal-generating means and the second initial reference value is predetermined from a control reaction using the second target nucleic acid sequence and the second signal-generating means; and
   (c) identifying whether the extracted signal satisfies an accuracy criterion; when the extracted signal does not satisfy the accuracy criterion, the step (b) is repeated, using an amended reference value instead of the initial reference value to re-extract the signal for the first target nucleic acid sequence or the second target nucleic acid sequence; wherein the amended reference value is determined such that the re-extracted signal satisfies the accuracy criterion.

2. The method of claim 1, wherein the accuracy criterion is that the extracted signal does not cross a predetermined threshold and the amended reference value is determined such that the re-extracted signal does not cross the predetermined threshold.

3. The method of claim 1, wherein the accuracy criterion is that the extracted signal has a signal value of more than a predetermined threshold and the amended reference value is determined such that the re-extracted signal has a signal value of more than the predetermined threshold.

4. The method of claim 3, wherein the amended reference value is determined as a value lower than the initial reference value.

5. The method of claim 1, wherein the accuracy criterion is that the extracted signal has a signal value of less than a predetermined threshold and the amended reference value is determined such that the re-extracted signal has a signal value of less than the predetermined threshold.

6. The method of claim 5, wherein the amended reference value is determined as a value higher than the initial reference value.

7. The method of claim 1, the amended reference value is determined by increasing or decreasing the initial reference value with a value interval until re-extracted signal satisfies the accuracy criterion.

8. The method of claim 1, wherein the amended reference value is applied to all cycles of the signals in the step (a) instead of the initial reference value to re-extract, the signal for the first target nucleic acid sequence or the second target nucleic acid sequence.

9. The method of claim 1, wherein the amended reference value is determined by a relationship of change in signals detected at the relatively high detection temperature and the relatively low detection temperature obtained in the step (a).

10. The method of claim 9, wherein the amended reference value is determined by applying a predetermined threshold as the accuracy criterion to the extracted signal, identifying a point at which the extracted signal firstly crosses the predetermined threshold, selecting a cycle at or after the identified point, and calculating at the selected cycle the relationship of change in signals at the relatively high detection temperature and the relatively low detection temperature in the step (a).

11. The method of claim 10, wherein the amended reference value is applied to all cycles of the signals in the step (a) instead of the initial reference value to re-extract the signal for the first target nucleic acid sequence or the second target nucleic acid sequence.

12. The method of claim 9, wherein the amended reference value is determined by applying a predetermined threshold as the accuracy criterion to the extracted signal, identifying a point at which a signal value firstly crosses the predetermined threshold, selecting a cycle at or after the identified point, and calculating at the selected cycle the relationship of change in signals at the relatively high detection temperature and the relatively low detection temperature in the step (a); and a plurality of additional amended reference values are determined by calculating at the cycles before the selected cycle the relationship of change in signals at the relatively high detection temperature and the relatively low detection temperature in the step (a).

13. The method of claim 12, wherein the amended reference value is applied to the selected cycle of the signals in the step (a): and all cycles after the selected cycle of the signals in the step (a); and each of the additional amended reference values is applied to each cycle before the selected cycle of the signals in the step (a) instead of the initial reference value to re-extract the signal for the first target nucleic acid sequence or the second target nucleic acid sequence.

14. The method of claim 1, wherein the first signal-generating means generates signals at the relatively high detection temperature and the relatively low detection temperature and the second signal-generating means generates a signal at the relatively low detection temperature.

15. The method of claim 14, wherein the processing of the signal values in the step (b) is mathematically performed by using the first initial reference value to extract the signal for the second target nucleic acid sequence from the signals at the relatively low detection temperature in the step (a).

16. The method of claim 14, wherein the mathematical processing of the signal values in the step (b) is performed using the first initial reference value to extract the signal for the second target nucleic acid sequence from the signal at the relatively high detection temperature in the step (a).

17. The method of claim 1, wherein the two signal-generating means generate signals at the relatively high detection temperature and the relatively low detection temperature.

18. The method of claim 17, wherein the second initial reference value is greater than the first initial reference value; wherein (i) the processing of the signal values in the step (b) is mathematically performed to extract the signal for the second target nucleic acid sequence by the first initial reference value from the signal at the relatively low detection temperature; (ii) the processing of the signal values in the step (b) is mathematically performed to extract the signal for the second target nucleic acid sequence by the first initial reference value from the signal at the relatively high detection temperature in the step (a); (iii) the processing of the signal values in the step (b) is mathematically performed to extract the signal for the first target nucleic acid sequence by the second initial reference value from the signal at the relatively low detection temperature; or (iv) the processing of the signal values in the step (b) is mathematically performed to extract the signal for the first target nucleic acid sequence by the second initial reference value from the signal the signal at the relatively high detection temperature in the step (a).

19. The method of claim 18, wherein when the mathematical processing is performed according to (i), the accuracy criterion is that the extracted signal has a signal value of more than the threshold; wherein when the mathematical processing is performed according to (ii), the accuracy criterion is that the extracted signal has a signal value of less than the threshold; wherein when the mathematical processing is performed according to (iii), the accuracy criterion is that the extracted signal has a signal value of less than the threshold; or wherein when the mathematical processing is performed according to (iv), the accuracy criterion is that the extracted signal has a signal value of more than the threshold.

20. A computer readable storage medium containing instructions to configure a processor to perform a method for extracting a signal for a target nucleic acid sequence from signals for two target nucleic acid sequences comprising a first target nucleic acid sequence and a second target nucleic acid sequence in a sample, the method comprising:
 (a) receiving signals from the sample at a relatively high detection temperature and a relatively low detection temperature; wherein the first target nucleic acid sequence in the sample is detected by a first signal-generating means and the second target nucleic acid sequence in the sample is detected by a second signal-generating means; wherein the detection is performed at one or more cycles of the signal-generating process to obtain a signal value at each of the one or more cycles; and wherein the two signals to be generated by the two signal-generating means are not differentiated by a single type of detector;
 (b) mathematically processing the signal values obtained in the step (a) by:
 using a second initial reference value to extract the signal for the first target nucleic acid sequence, or
 using a first initial reference value to extract the signal for the second target nucleic acid sequence; wherein the first initial reference value is a value representing a relationship of change in signals provided by the first signal-generating means at the relatively high detection temperature and the relatively low detection temperature, and the second initial reference value is a value representing a relationship of change in signals provided by the second signal-generating means at the relatively high detection temperature and the relatively low detection temperature; and wherein the first initial reference value is predetermined from a separate reaction using the first target nucleic acid sequence and the first signal-generating means and, the second initial reference value is predetermined from a separate reaction using the second target nucleic acid sequence and the second signal-generating means; and
 (c) identifying whether the extracted signal satisfies an accuracy criterion; when the extracted signal does not satisfy the accuracy criterion, the step (b) is repeated using an amended reference value instead of the initial reference value to re-extract the signal for the first target nucleic acid sequence or the second target nucleic acid sequence; wherein the amended reference value is determined such that the re-extracted signal satisfies the accuracy criterion.

21. A device for extracting a signal for a target nucleic acid sequence from signals for two target nucleic acid sequences comprising a first target nucleic acid sequence and a second target nucleic acid sequence in a sample, comprising (a) a computer processor and (b) the computer readable storage medium of claim 20 coupled to the computer processor.

22. A computer program to be stored on a computer readable storage medium to configure a processor to perform a method for extracting a signal for a target nucleic acid sequence from signals for two target nucleic acid sequences comprising a first target nucleic acid sequence and a second target nucleic acid sequence in a sample, the method comprising:

(a) receiving signals from the sample at a relatively high detection temperature and a relatively low detection temperature; wherein the first target nucleic acid sequence in the sample is detected by a first signal-generating means and the second target nucleic acid sequence in the sample is detected by a second signal-generating means; wherein the detection is performed at one or more cycles of the signal-generating process to obtain a signal value at each of the one or more cycles; and wherein the two signals to be generated by the two signal-generating means are not differentiated by a single type of detector;

(b) processing the signal values obtained in the step (a) by:

using a second initial reference value to extract the signal for the first target nucleic acid sequence, or using a first initial reference value to extract the signal for the second target nucleic acid sequence;

wherein the first initial reference value is a value representing a relationship of change in signals provided by the first signal-generating means at the relatively high detection temperature and the relatively low detection temperature, and the second initial reference value is a value representing a relationship of change in signals provided by the second signal-generating means at the relatively high detection temperature and the relatively low detection temperature; and wherein the first initial reference value is predetermined from a separate reaction using the first target nucleic acid sequence and the first signal-generating means and the second initial reference value is predetermined from a separate reaction using the second target nucleic acid sequence and the second signal-generating means; and (c) identifying whether the extracted signal satisfies an accuracy criterion; when the extracted signal does not satisfy the accuracy criterion, the step (b) is repeated using an amended reference value instead of the initial reference value to re-extract the signal for the first target nucleic acid sequence or the second target nucleic acid sequence; wherein the amended reference value is determined such that the re-extracted signal satisfies the accuracy criterion.

* * * * *

SEQUENCE LISTING

<160> NUMBER OF SEQ ID NOS: 12

<210> SEQ ID NO 1
<211> LENGTH: 37
<212> TYPE: DNA
<213> ORGANISM: Artificial Sequence
<220> FEATURE:
<223> OTHER INFORMATION: Primer Forward Neisseria gonorrhoeae (NG_F)
<220> FEATURE:
<221> NAME/KEY: misc_feature
<222> LOCATION: (22)..(26)
<223> OTHER INFORMATION: n denotes deoxyinosine

<400> SEQUENCE: 1
tacgcctgct actttcacgc tnnnnngtaa tcagatg                              37

<210> SEQ ID NO 2
<211> LENGTH: 37
<212> TYPE: DNA
<213> ORGANISM: Artificial Sequence
<220> FEATURE:
<223> OTHER INFORMATION: Primer Reverse Neisseria gonorrhoeae (NG_R)
<220> FEATURE:
<221> NAME/KEY: misc_feature
<222> LOCATION: (22)..(26)
<223> OTHER INFORMATION: n denotes deoxyinosine

<400> SEQUENCE: 2
caatggatcg gtatcactcg cnnnnncgag caagaac                              37

<210> SEQ ID NO 3
<211> LENGTH: 34
<212> TYPE: DNA
<213> ORGANISM: Artificial Sequence
<220> FEATURE:
<223> OTHER INFORMATION: Primer Probing and Tagging 25 Oligonucleotide
      (NG_PTO)

<400> SEQUENCE: 3
gtacgcgata cgggcccctc attggcgtgt ttcg                                 34

<210> SEQ ID NO 4
<211> LENGTH: 39
<212> TYPE: DNA
<213> ORGANISM: Artificial Sequence
<220> FEATURE:
<223> OTHER INFORMATION: Primer Capturing and Templating Oligonucleotide
      (NG_CTO)

<400> SEQUENCE: 4 ttttttttt ttttttttg tactgcccgt atcgcgtac                              39

<210> SEQ ID NO 5
<211> LENGTH: 40
<212> TYPE: DNA
<213> ORGANISM: Artificial Sequence
<220> FEATURE:
<223> OTHER INFORMATION: Primer Forward Chlamydia trachomatis (CT_F)
<220> FEATURE:
<221> NAME/KEY: misc_feature
<222> LOCATION: (26)..(30)
<223> OTHER INFORMATION: n denotes deoxyinosine

<400> SEQUENCE: 5
gagttttaaa atgggaaatt ctggtnnnnn tttgtataac                           40

<210> SEQ ID NO 6
<211> LENGTH: 40

```
<212> TYPE: DNA
<213> ORGANISM: Artificial Sequence
<220> FEATURE:
<223> OTHER INFORMATION: Primer Reverse Chlamydia trachomatis (CT_R)
<220> FEATURE:
<221> NAME/KEY: misc_feature
<222> LOCATION: (26)..(30)
<223> OTHER INFORMATION: n denotes deoxyinosine

<400> SEQUENCE: 6
ccaattgtaa tagaagcatt ggttgnnnnn ttattggaga                                40

<210> SEQ ID NO 7
<211> LENGTH: 39
<212> TYPE: DNA
<213> ORGANISM: Artificial Sequence
<220> FEATURE:
<223> OTHER INFORMATION: Primer Probing and Tagging 25 Oligonucleotide
      CT_PTO

<400> SEQUENCE: 7
gattacgcga ccgcatcaga agctgtcatt ttggctgcg                                 39

<210> SEQ ID NO 8
<211> LENGTH: 39
<212> TYPE: DNA
<213> ORGANISM: Artificial Sequence
<220> FEATURE:
<223> OTHER INFORMATION: Primer Capturing and Templating Oligonucleotide
      CT_CTO

<400> SEQUENCE: 8
gcgctggata ccctggacga tatgtgcggt cgcgtaatc                                 39

<210> SEQ ID NO 9
<211> LENGTH: 22
<212> TYPE: DNA
<213> ORGANISM: Artificial Sequence
<220> FEATURE:
<223> OTHER INFORMATION: Taqman Probe NG_P

<400> SEQUENCE: 9
tgcccctcat tggcgtgttt cg                                                   22

<210> SEQ ID NO 10
<211> LENGTH: 36
<212> TYPE: DNA
<213> ORGANISM: Artificial Sequence
<220> FEATURE:
<223> OTHER INFORMATION: Primer Forward CT2_F
<220> FEATURE:
<221> NAME/KEY: misc_feature
<222> LOCATION: (22)..(26)
<223> OTHER INFORMATION: n denotes deoxyinosine

<400> SEQUENCE: 10
tccgaatgga taaagcgtga cnnnnnatga actcac                                    36

<210> SEQ ID NO 11
<211> LENGTH: 37
<212> TYPE: DNA
<213> ORGANISM: Artificial Sequence
<220> FEATURE:
<223> OTHER INFORMATION: Primer Reverse CT2_R
<220> FEATURE:
<221> NAME/KEY: misc_feature
<222> LOCATION: (23)..(27)
<223> OTHER INFORMATION: n denotes deoxyinosine
```

```
<400> SEQUENCE: 11
aacaatgaat cctgagcaaa ggnnnnncgt tagagtc                                    37

<210> SEQ ID NO 12
<211> LENGTH: 29
<212> TYPE: DNA
<213> ORGANISM: Artificial Sequence
<220> FEATURE:
<223> OTHER INFORMATION: Taqman Probe CT2_P

<400> SEQUENCE: 12
cattgtaaag atatggtctg cttcgaccg                                             29
```